(12) United States Patent
Asher et al.

(10) Patent No.: US 11,278,340 B2
(45) Date of Patent: Mar. 22, 2022

(54) COMBINATION ULTRASONIC AND ELECTROSURGICAL INSTRUMENT WITH ADJUSTABLE ENERGY MODALITIES AND METHOD FOR SEALING TISSUE AND INHIBITING TISSUE RESECTION

(71) Applicant: Ethicon LLC, Guaynabo, PR (US)

(72) Inventors: Ryan M. Asher, Cincinnati, OH (US); Benjamin J. Danziger, Cincinnati, OH (US); Kristen G. Denzinger, Cincinnati, OH (US); Cameron R. Nott, Loveland, OH (US); Amrita S. Sawhney, Cincinnati, OH (US); Eitan T. Wiener, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 616 days.

(21) Appl. No.: 15/967,763

(22) Filed: May 1, 2018

(65) Prior Publication Data

US 2018/0333185 A1 Nov. 22, 2018

Related U.S. Application Data

(60) Provisional application No. 62/509,336, filed on May 22, 2017.

(51) Int. Cl.
*A61B 18/14* (2006.01)
*A61B 18/00* (2006.01)
(Continued)

(52) U.S. Cl.
CPC ...... *A61B 18/00* (2013.01); *A61B 17/320092* (2013.01); *A61B 18/1233* (2013.01);
(Continued)

(58) Field of Classification Search
CPC .... A61B 17/320068; A61B 17/320092; A61B 2017/00026; A61B 2017/00084;
(Continued)

(56) References Cited

U.S. PATENT DOCUMENTS 5,322,055 A 6/1994 Davison et al.
5,792,135 A 8/1998 Madhani et al.
(Continued)

FOREIGN PATENT DOCUMENTS

EP 1 839 599 A1 10/2007

OTHER PUBLICATIONS

International Search Report and Written Opinion for International Application No. PCT/US2018/033301, dated Jul. 30, 2018, 13 pgs.
(Continued)

*Primary Examiner* — Khadijeh A Vahdat
(74) *Attorney, Agent, or Firm* — Frost Brown Todd LLC

(57) ABSTRACT

An ultrasonic surgical instrument and method of sealing tissue includes interrogating the tissue with an electrical signal and adjusting an electrical parameter of at least one of the ultrasonic energy or the RF energy in response to the tissue feedback to inhibit transecting the tissue. The ultrasonic surgical instrument has an end effector, a shaft assembly, a body, and a power controller. The power controller is operatively connected to the ultrasonic blade and the RF electrode and configured to direct activation of the ultrasonic blade or the RF electrode. The power controller is further configured to interrogate the tissue with the electrical signal via the ultrasonic blade or the RF electrode to provide a tissue feedback and adjust an electrical parameter of the ultrasonic energy or the RF energy in response to the tissue feedback to inhibit transecting the tissue.

20 Claims, 17 Drawing Sheets

(51) Int. Cl.
*A61B 17/32* (2006.01)
*A61B 18/12* (2006.01)
*A61B 17/00* (2006.01)
*A61B 90/00* (2016.01)

(52) U.S. Cl.
CPC .. *A61B 18/1445* (2013.01); *A61B 2017/0019* (2013.01); *A61B 2017/00026* (2013.01); *A61B 2017/00084* (2013.01); *A61B 2017/00106* (2013.01); *A61B 2017/00526* (2013.01); *A61B 2017/320075* (2017.08); *A61B 2017/320088* (2013.01); *A61B 2017/320094* (2017.08); *A61B 2017/320095* (2017.08); *A61B 2018/0063* (2013.01); *A61B 2018/00607* (2013.01); *A61B 2018/00642* (2013.01); *A61B 2018/00648* (2013.01); *A61B 2018/00654* (2013.01); *A61B 2018/00672* (2013.01); *A61B 2018/00678* (2013.01); *A61B 2018/00702* (2013.01); *A61B 2018/00708* (2013.01); *A61B 2018/00714* (2013.01); *A61B 2018/00755* (2013.01); *A61B 2018/00761* (2013.01); *A61B 2018/00779* (2013.01); *A61B 2018/00875* (2013.01); *A61B 2018/00916* (2013.01); *A61B 2018/00928* (2013.01); *A61B 2018/00994* (2013.01); *A61B 2018/126* (2013.01); *A61B 2018/1452* (2013.01); *A61B 2090/064* (2016.02)

(58) Field of Classification Search
CPC .. A61B 2017/00106; A61B 2017/0019; A61B 2017/00526; A61B 2017/320075; A61B 2017/320088; A61B 2017/320094; A61B 2017/320095; A61B 18/00; A61B 18/1233; A61B 18/1442; A61B 18/1445; A61B 2018/00607; A61B 2018/0063; A61B 2018/00642; A61B 2018/00648; A61B 2018/00654; A61B 2018/00672; A61B 2018/00678; A61B 201/00702; A61B 2018/00708; A61B 2018/00714; A61B 2018/00755; A61B 2018/00761; A61B 2018/00779; A61B 2018/00791; A61B 2018/00845; A61B 2018/00875; A61B 2018/0088; A61B 2018/00916; A61B 2018/00928; A61B 2018/00994; A61B 2018/126; A61B 2018/1452; A61B 2018/1457; A61B 2018/1467; A61B 2090/064
USPC .............................. 606/51–52, 169, 205–207
See application file for complete search history.

(56) References Cited

U.S. PATENT DOCUMENTS

| | | | |
|---|---|---|---|
| 5,817,084 A | 10/1998 | Jensen | |
| 5,873,873 A | 2/1999 | Smith et al. | |
| 5,878,193 A | 3/1999 | Wang et al. | |
| 5,980,510 A | 11/1999 | Tsonton et al. | |
| 6,231,565 B1 | 5/2001 | Tovey et al. | |
| 6,283,981 B1 | 9/2001 | Beaupre et al. | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,500,176 B1 | 12/2002 | Truckai et al. | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,057,498 B2 | 11/2011 | Robertson | |
| 8,366,727 B2 | 2/2013 | Witt et al. | |
| 8,460,326 B2 | 6/2013 | Houser et al. | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV et al. | |
| 8,844,789 B2 | 9/2014 | Shelton, IV et al. | |
| 8,939,974 B2 | 1/2015 | Boudreaux et al. | |
| 9,044,261 B2 | 6/2015 | Houser | |
| 9,089,327 B2 | 7/2015 | Worrell et al. | |
| 9,161,803 B2 | 10/2015 | Yates et al. | |
| 9,192,431 B2 | 11/2015 | Woodruff et al. | |
| 9,237,921 B2 | 1/2016 | Messerly et al. | |
| 9,301,759 B2 | 4/2016 | Spivey et al. | |
| 9,402,682 B2 | 8/2016 | Worrell et al. | |
| 9,439,668 B2 | 9/2016 | Timm et al. | |
| 9,545,253 B2 | 1/2017 | Worrell et al. | |
| 9,572,622 B2 | 2/2017 | Shelton, IV et al. | |
| 9,681,884 B2 | 6/2017 | Clem et al. | |
| 9,724,118 B2 | 8/2017 | Schulte et al. | |
| 10,617,463 B2 | 4/2020 | McHenry et al. | |
| 10,813,684 B2 | 10/2020 | Worrell et al. | |
| 2010/0036405 A1* | 2/2010 | Giordano ............. | A61B 5/6847 606/169 |
| 2011/0087212 A1 | 4/2011 | Aldridge et al. | |
| 2012/0078243 A1 | 3/2012 | Worrell et al. | |
| 2012/0116379 A1* | 5/2012 | Yates ................... | H01M 10/48 606/33 |
| 2012/0116391 A1 | 5/2012 | Houser et al. | |
| 2015/0141981 A1 | 5/2015 | Price et al. | |
| 2015/0257780 A1 | 9/2015 | Houser et al. | |
| 2016/0022305 A1 | 1/2016 | Lamping et al. | |
| 2016/0058492 A1* | 3/2016 | Yates ................. | A61B 18/1206 606/34 |
| 2016/0270840 A1 | 9/2016 | Yates et al. | |
| 2017/0000516 A1 | 1/2017 | Stulen et al. | |
| 2017/0000541 A1 | 1/2017 | Yates et al. | |
| 2017/0000542 A1 | 1/2017 | Yates et al. | |
| 2017/0000554 A1 | 1/2017 | Yates et al. | |
| 2017/0056056 A1 | 3/2017 | Wiener et al. | |

OTHER PUBLICATIONS

International Search Report and Written Opinion for International Application No. PCT/US2018/033303, dated Jan. 24, 2019, 20 pgs.
U.S. Appl. No. 62/509,336, entitled "Control Algorithm for Surgical Instrument With Ultrasonic and Electrosurgical Modaliiies," filed May 22, 2017.
International Search Report and Written Opinion for International Application No. PCT/US2018/033305, dated Aug. 23, 2018, 16 pages.
International Search Report and Written Opinion for International Application No. PCT/US2018/033306, dated Sep. 3, 2018, 17 pages.
International Search Report and Written Opinion for International Application No. PCT/US2018/033309, dated Aug. 17, 2018, 16 pages.

(56) References Cited

OTHER PUBLICATIONS

International Search Report and Written Opinion for International Application No. PCT/US2018/033311, dated Aug. 23, 2018, 16 pages.
U.S. Appl. No. 15/967,740, entitled "Combination Ultrasonic and Electrosurgical Instrument Having Electrical Circuits with Shared Return Path," filed May 1, 2018.
U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,758, entitled "Combination Ultrasonic and Electrosurgical Instrument with Clamp Arm Position Input and Method for Identifying Tissue State," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,764, entitled "Combination Ultrasonic and Electrosurgical System Having EEPROM and ASIC Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.
U.S. Appl. No. 62/509,351, entitled "Ultrasonic Instrument with Electrosurgical Features," filed May 22, 2017.
U.S. Appl. No. 15/967,758.
U.S. Appl. No. 15/967,770.
U.S. Appl. No. 15/967,775.
U.S. Appl. No. 15/967,777.
U.S. Appl. No. 15/967,784.
European Examination Report dated Jun. 28, 2021 for Application No. EP 18729278.4, 4 pgs.
European Examination Report dated Jun. 29, 2021 for Application No. EP 18731583.3, 4 pgs.
European Examination Report dated Jun. 29, 2021 for Application No. EP 18731584.1, 4 pgs.
European Examination Report dated Jun. 30, 2021 for Application No. EP 18731585.8, 4 pgs.

* cited by examiner

COMBINATION ULTRASONIC AND ELECTROSURGICAL INSTRUMENT WITH ADJUSTABLE ENERGY MODALITIES AND METHOD FOR SEALING TISSUE AND INHIBITING TISSUE RESECTION

CROSS-REFERENCE TO RELATED APPLICATION

This application claims priority to U.S. Provisional Pat. App. No. 62/509,336, entitled "Control Algorithm for Surgical Instrument with Ultrasonic and Electrosurgical Modalities," filed May 22, 2017, the disclosure of which is incorporated by reference herein.

BACKGROUND

Ultrasonic surgical instruments utilize ultrasonic energy for both precise cutting and controlled coagulation. Ultrasonic energy cuts and coagulates by vibrating a blade in contact with tissue. Vibrating at frequencies of approximately 55.5 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit such energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, issued as U.S. Pat. No. 11,141,213 on Oct. 12, 2021, the disclosure of which is incorporated by reference herein.

While various types of ultrasonic surgical instruments and electrosurgical instruments, including combination ultrasonic-electrosurgical devices, have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
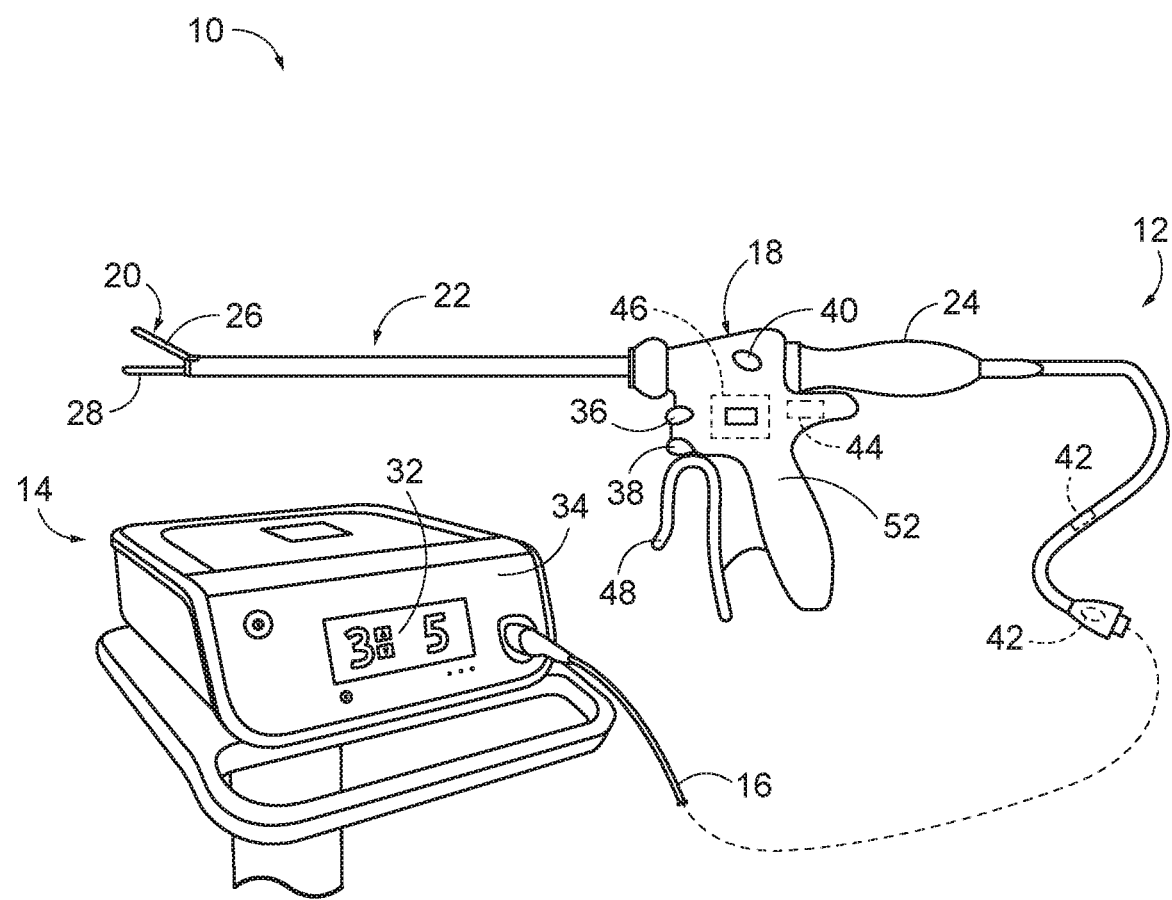
FIG. 1 depicts a schematic view of an exemplary ultrasonic surgical instrument including a shaft assembly and a handle assembly operatively connected to an ultrasonic generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical System

FIG. 1 illustrates one example of a surgical system (10) including a surgical instrument (12) and a generator (14) coupled via a cable (16). Surgical instrument (12) has a proximally positioned handle assembly (18), which may also be referred to as a handpiece, a distally positioned end effector (20), a shaft assembly (22) extending therebetween, and an ultrasonic transducer (24). End effector (20) generally includes a clamp arm (26) pivotally connected relative to an ultrasonic blade (28) and configured to pivot from an open position of an open configuration to a closed position of a closed configuration as discussed below in greater detail. Ultrasonic blade (28) is acoustically coupled with ultrasonic transducer (24) via an acoustic waveguide (not shown) for providing ultrasonic energy to ultrasonic blade (28). In addition, end effector (20) further includes a plurality of RF electrodes (30) positioned therealong for contacting the tissue in either the open or closed position as desired by a clinician. Generator (14) operatively connects to ultrasonic blade (28) and RF electrodes (30) to respectively provide ultrasonic energy and RF energy to ultrasonic blade (28) and RF electrodes (30) to thereby cut and/or seal the tissue is use.

In some versions, clamp arm (26) has two or more electrodes (30). In some such versions, electrodes (30) of clamp arm are capable of applying bipolar RF energy to tissue. In some such versions, ultrasonic blade (28) remains electrically neutral, such that ultrasonic blade (28) is not part of the RF circuit. In some other versions, ultrasonic blade (28) forms part of the RF circuit, such that ultrasonic blade (28) cooperates with one or more electrodes (30) of clamp arm (26) to apply bipolar RF energy to tissue. By way of example only, some versions of clamp arm (26) may have just one electrode (30) that serves as an active pole for RF energy; while ultrasonic blade (28) provides a return pole for RF energy. Thus, the term "electrodes (30)" should be read to include versions where clamp arm (26) has only one single electrode.

It should be understood that terms such as "proximal" and "distal" are used herein with reference to surgical instrument (12). Thus, end effector (20) is distal with respect to the more proximal handle assembly (18). It will be further appreciated that for convenience and clarity, spatial terms such as "upper" and "lower" are used herein with respect to the drawings. However, surgical instruments are used in many orientations and positions, and these terms are not intended to be limiting and absolute. Likewise, terms such as "instrument" and "device" as well as "limit" and "cap" may be used interchangeably.

A. Exemplary Generator

With reference to FIG. 1, generator (14) drives a combination surgical instrument (12) with both ultrasonic and RF energies. Generator (14) is shown separate from surgical instrument (12) in the present example, but, alternatively, generator (14) may be formed integrally with surgical instrument (12) to form a unitary surgical system. Generator (14) generally includes an input device (32) located on a front panel (34) of generator (14). Input device (32) may have any suitable device that generates signals suitable for programming the operation of generator (32). For example, in operation, the clinician may program or otherwise control operation of generator (32) using input device (32) (e.g., by one or more processors contained in the generator) to control the operation of generator (14) (e.g., operation of the ultrasonic generator drive circuit (not shown) and/or RF generator drive circuit (not shown)).

In various forms, input device (32) includes one or more buttons, switches, thumbwheels, keyboard, keypad, touch screen monitor, pointing device, remote connection to a general purpose or dedicated computer. In other forms, input device (32) may having a suitable user interface, such as one or more user interface screens displayed on a touch screen monitor. Accordingly, the clinician may selectively set or program various operating parameters of the generator, such as, current (I), voltage (V), frequency (f), and/or period (T) of a drive signal or signals generated by the ultrasonic and RF generator drive circuits (not shown). Specifically, in the present example, generator (32) is configured to deliver various power states to the surgical instrument (10) that include, but are not necessarily limited to, only ultrasonic energy, only RF energy, and a combination of ultrasonic and RF energies, which simultaneously powers ultrasonic blade (28) and RF electrodes (30). It will be appreciated that input device (32) may have any suitable device that generates signals suitable for programming the operation of generator (14) and should not be unnecessarily limited to input device (32) shown and described herein.

By way of example only, generator (14) may comprise a GEN04 or GEN11 sold by Ethicon Endo-Surgery, Inc. of Cincinnati, Ohio. In addition, or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

B. Exemplary Surgical Instrument

Surgical instrument (10) of the present example shown in FIG. 1 includes a plurality of energy inputs, which are more particularly referred to herein as an upper button (36), lower button (38), and side button (40). By way of example, upper button (36) is configured to direct generator (14) to power ultrasonic transducer (24) with a maximum ultrasonic energy output, whereas lower button (38) is configured to direct generator (14) to power ultrasonic transducer (24) with a lower ultrasonic energy output. By way of further example, side button (40) is configured to direct generator (14) to power ultrasonic transducer (24) with a pulsed energy output, such as 5 continuous signals and 5 or 4 or 3 or 2 or 1 pulsed signals. In one or more examples, the specific drive signal configuration directed by energy inputs may be controlled and/or based upon EEPROM settings in generator (14) and/or user power level selection(s). By way of further example, surgical instrument (10) may include a two-button configuration for selectively directing ultrasonic and RF energies as described herein. Various examples of instruments having two-button input configurations are described in various patent references cited herein. In any case, it will be appreciated that the invention described herein is not intended to be unnecessarily limited to a particular input button, switch, etc. to the extent that any form of input may be so used.

Surgical instrument (12) further includes a first data circuit (42) and a second data circuit (44) in communication with generator (14). For example, first data circuit (42) indicates a burn-in frequency slope. Additionally or alternatively, any type of information may be communicated to second data circuit (42) for storage therein via a data circuit interface (e.g., using a logic device). Such information may comprise, for example, an updated number of operations in which surgical instrument (12) has been used and/or dates and/or times of its usage. In other examples, second data circuit (44) may transmit data acquired by one or more sensors (e.g., an instrument-based temperature sensor). In still other examples, second data circuit (44) may receive data from generator (14) and provide an indication to a clinician (e.g., an LED indication or other visible indication) based on the received data to and/or from surgical instrument (12). In the present example, second data circuit (44) stores information about the electrical and/or ultrasonic properties of an associated transducer (24) and/or end effector (20), which includes data measured and collected from ultrasonic blade (28) and/or RF electrodes (30).

To this end, various processes and techniques described herein are performed by a controller (46), which includes internal logic. In one example, controller (46) has at least one processor and/or other controller device in communication with generator (14), ultrasonic blade (28), RF electrodes (30), and other inputs and outputs described herein for monitoring and performing such processes and techniques. In one example, controller (46) has a processor configured to monitor user input provided via one or more inputs and capacitive touch sensors. Controller (46) may also include a touch screen controller to control and manage the acquisition of touch data from a capacitive touch screen.

Figure 2A:
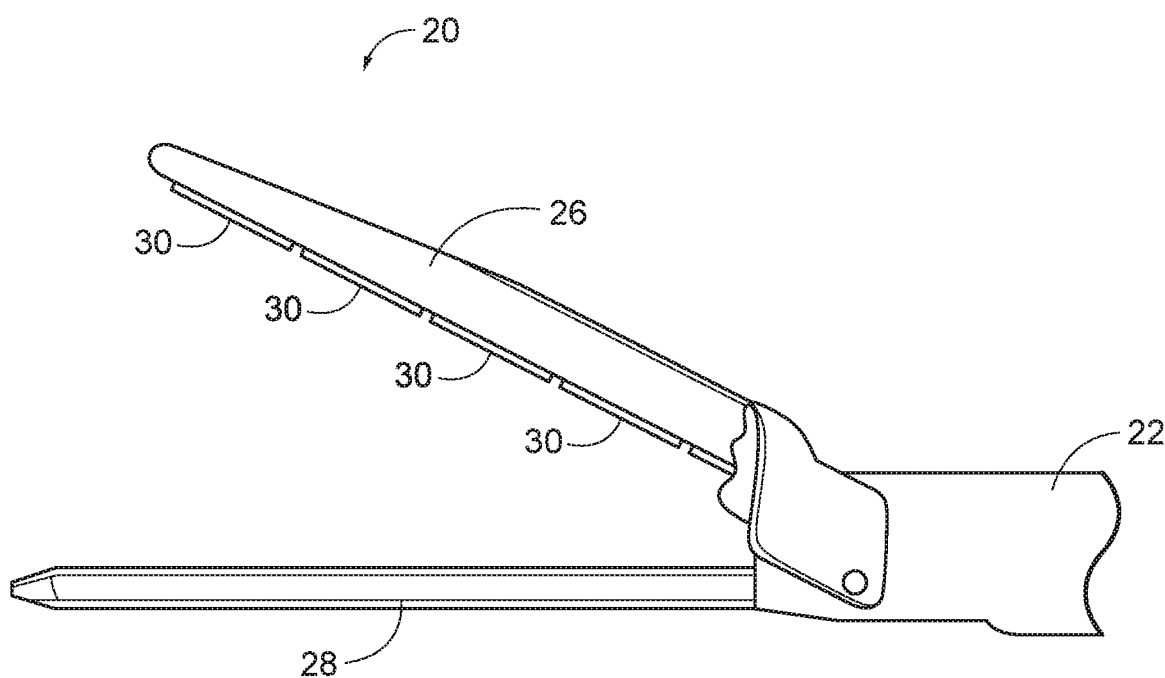
FIG. 2A depicts a side view of an end effector of the ultrasonic surgical instrument of FIG. 1 showing the end effector in an open configuration for receiving tissue of a patient.
Figure 2B:
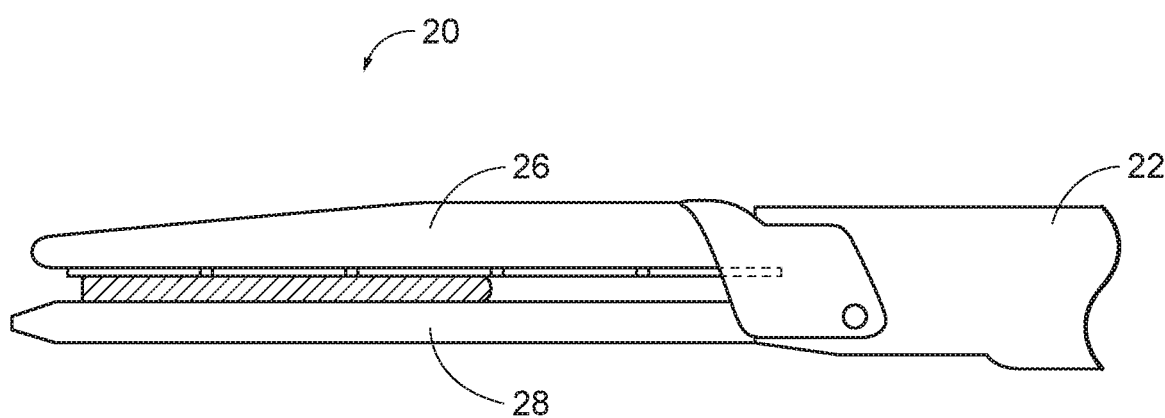
FIG. 2B depicts the side view of the end effector of FIG. 2A, but with the end effector in a closed configuration for clamping the tissue of the patient.

With reference to FIGS. 1-2B, handle assembly (18) further includes a trigger (48) operatively connected to clamp arm (26). Trigger (48) and clamp arm (26) are generally biased toward the unactuated, open configuration. However, selectively manipulating trigger (48) proximally pivots clamp arm (26) toward ultrasonic blade (28) from the open position to the closed position. As used in the present example, clamp arm (26) and ultrasonic blade (28) may also be generally referred to respectively as upper and lower jaws of surgical instrument (12). In the open position, clamp arm (26) and ultrasonic blade (28) are configured to receive the tissue, whereas clamp arm (26) is configured to clamp tissue against ultrasonic blade (28) for grasping, sealing, and/or cutting the tissue.

Ultrasonic blade (28) ultrasonically vibrates to seal and/or cut the tissue, whereas RF electrodes (30) provide electrical power to the tissue. RF electrodes (30) of the present example are all electrically similar electrodes with ultrasonic blade (28) also electrically connected as a return electrode. As used therein, the term "electrode" may thus apply to both RF electrodes (30) and ultrasonic blade (28) with respect to the RF electrical circuit. Without tissue, the electrical circuit from RF electrodes (30) to ultrasonic blade (28) is open, whereas the electrical circuit is closed by the tissue between RF electrode (30) and ultrasonic blade (28) in use. RF electrodes (30) may be activated to apply RF energy alone or in combination with ultrasonic activation of ultrasonic blade (28). For example, activating only RF electrodes (30) to apply RF energy alone may be used for spot coagulating without concern for inadvertently cutting tissue with ultrasonically activated ultrasonic blade (28). However, the combination of ultrasonic energy and RF energy may be used for sealing and/or cutting tissue to achieve any combination of diagnostic or therapeutic effects, various examples of which will be described below in greater detail.

As noted above, generator (14) is a single output generator that can deliver power through a single port to provide both RF and ultrasonic energy such that these signals can be delivered separately or simultaneously to end effector (20) for cutting and/or sealing tissue. Such a single output port generator (14) has a single output transformer with multiple taps to provide power, either for RF or for ultrasonic energy, to end effector (20) depending on the particular treatment being performed on the tissue. For example, generator (14) may deliver energy with higher voltage and lower current to drive ultrasonic transducer (24), with lower voltage and higher current as required to drive RF electrodes (30) for sealing tissue, or with a coagulation waveform for spot coagulation using either monopolar or bipolar electrosurgical electrodes. The output waveform from generator (14) can be steered, switched, or filtered to provide the desired frequency to end effector (20) of surgical instrument (12).

II. Operation of Surgical System for Interrogating and Sealing Tissue

Surgical system (10) is configured for cutting and/or sealing tissue as discussed above with respect to FIGS. 1-2B. The particular diagnostic and/or therapeutic effects associated with various treatments may be adjusted in use with controller (46) monitoring, directing, and adjusting aspects of the ultrasonic and RF energies in conjunction with one or more tissue properties, which may even change for adjustment in real-time.

Figure 3:
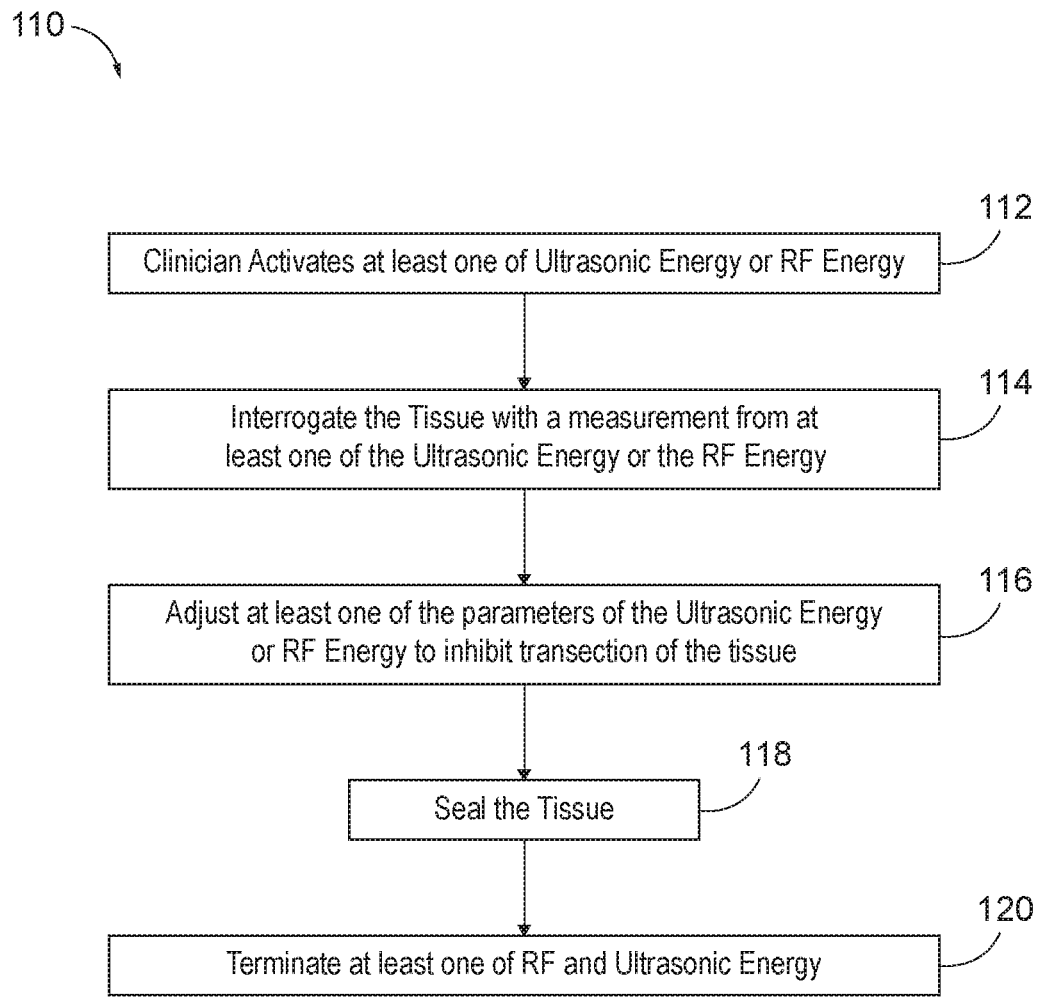
FIG. 3 depicts a flowchart of a high-level method of interrogating and sealing the tissue with the ultrasonic surgical instrument of FIG. 1.

Generally, with respect to FIG. 1 and FIG. 3, a high-level method (110) of interrogating and sealing tissue with surgical system (10) includes a step (112) of activating at least one of the ultrasonic energy or the RF energy as discussed above. During step (112), end effector (20) contacts tissue for treatment. Controller (46) directs interrogation of the tissue during a step (114) from at least one of the ultrasonic and RF energies applied respectively to the tissue by ultrasonic blade (28) and RF electrodes (30). Controller (46) monitors interrogation and receives feedback from step (114) with respect to a tissue parameter, also referred to herein as tissue feedback. In response, controller (46) adjusts at least one electrical parameter of one of the ultrasonic and RF energies to inhibit transaction of the tissue in a step (116). At least one of the ultrasonic and RF energies remains activated until the tissue is sealed in a step (118), but not transected. Once sealed in step (118), the ultrasonic and RF energies are terminated from active to inactive in a step (120).

With respect to step (112) through step (120), as with respect to other steps described below, controller (46) is generally configured to direct such methods and processes described herein for the operation of surgical system (10). While controller (46) may not be explicitly mentioned as providing such direction for each step, it will be appreciated that controller (46), or alternative device for providing direction, may be so used. In addition, various steps may be performed alone, in combination, or exchanged with like steps. For example, tissue interrogation of step (112) and parameter adjustment (116) represent high-level method steps with more particular versions thereof being capable of being performed alone, in combination, or exchanged with one another. The invention is thus not intended to be unnecessarily limited to the high-level methods of versions thereof with respect to order and number of steps.

Figure 4:
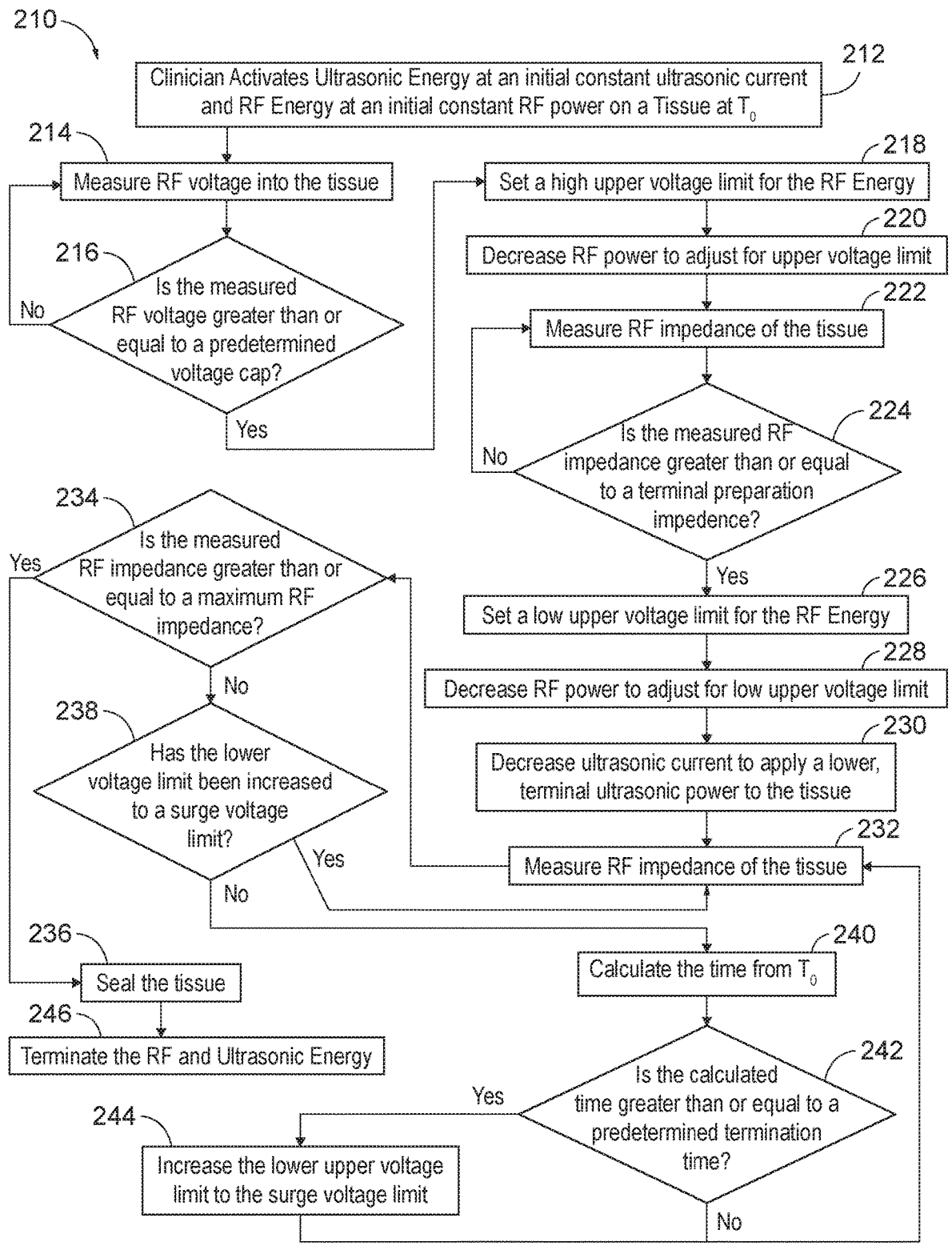
FIG. 4 depicts a flowchart for a first exemplary version of implementing the method of FIG. 3 with set voltage limits based on RF impedance.
Figure 5:
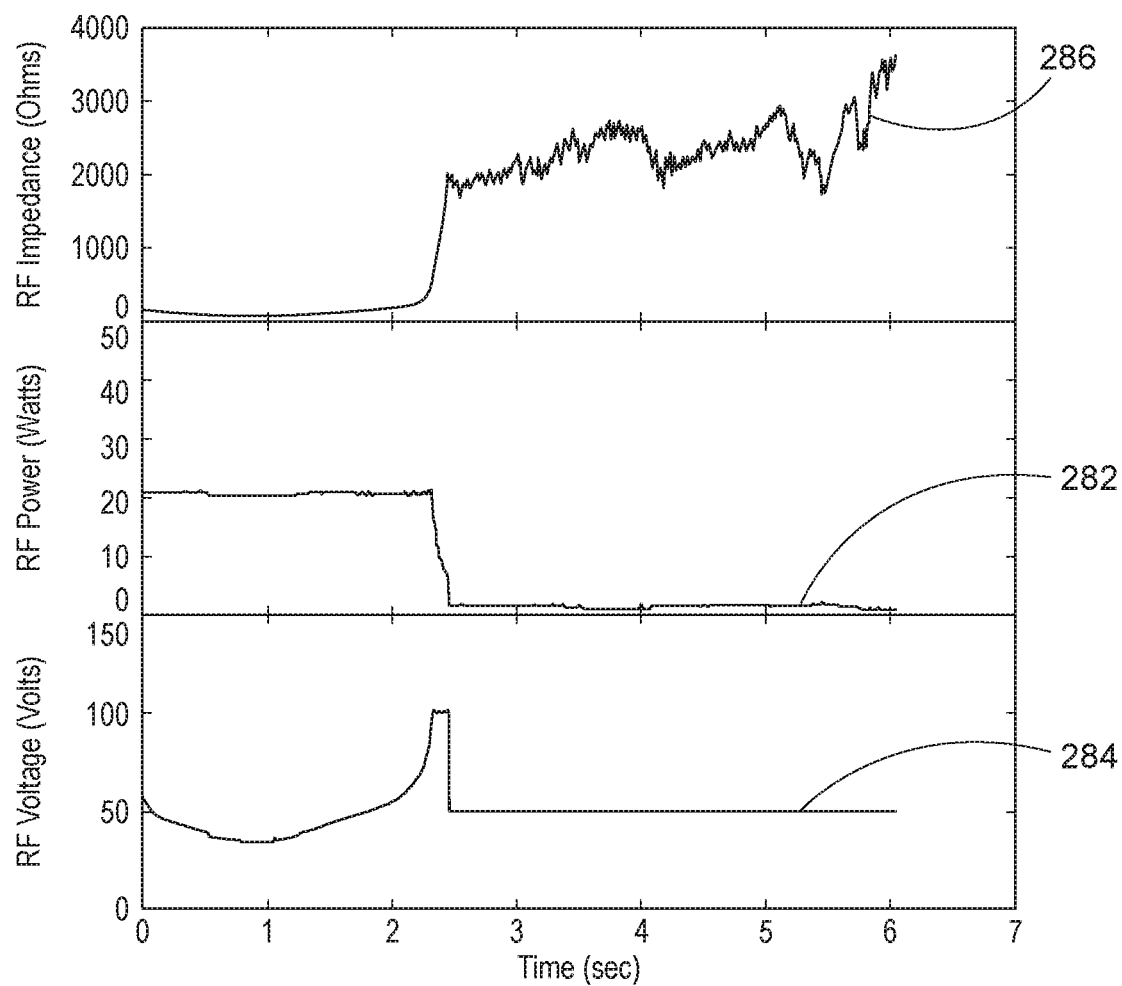
FIG. 5 depicts a graph of RF electrical circuit parameters during the first exemplary implementation of FIG. 4.
Figure 6:
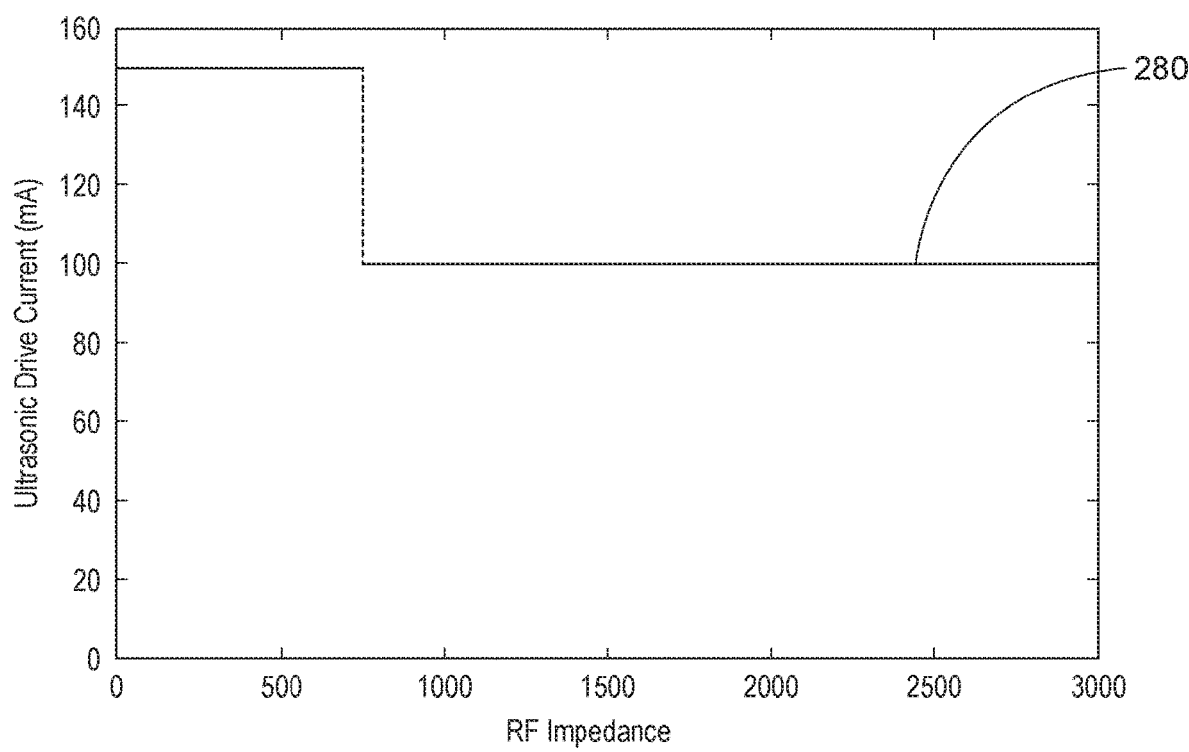
FIG. 6 depicts a graph of ultrasonic circuit electrical parameters during the first exemplary implementation of FIG. 4.

A. First Exemplary Version of Interrogating and Sealing Tissue with Set Voltage Limits Based on RF Impedance A first exemplary version for a method (210) of interrogating and sealing tissue with surgical system (10) of FIG. 1 is shown in FIGS. 4-6 in greater detail. The clinician activates ultrasonic and RF energies respectively at an initial ultrasonic power with a constant ultrasonic drive current (280) and an initial constant RF power (282), such as 20 watts, in a step (212). Furthermore, step (212) includes applying these ultrasonic and RF energies to the tissue via ultrasonic blade (28) and RF electrodes (30) at an initial time, $T_o$. At a step (214), controller (46) interrogates the tissue with a measurement of an RF voltage (284) of the tissue by RF electrodes (30). A predetermined voltage cap (220), such as 100 volts, is stored and accessible by controller (46) for comparison to the measured RF voltage (284) in step (216). In the event that the measured RF voltage (284) is less than the predetermined voltage cap in step (216), the initial ultrasonic and RF energies continue to be applied to the tissue. Application of the constant RF power to the tissue causes measured RF voltage to rise as an RF impedance (286) rises until the continuously measured RF voltage (284) is greater than or equal to the predetermined voltage cap. Once the measured RF voltage (284) is greater than or equal to the predetermined voltage cap in step (216), controller (46) sets a high upper voltage limit, such as 100 volts, on the RF energy applied to the tissue in a step (218).

In response to the high upper voltage limit of 100 volts, controller (46) directs a decrease of RF power (282) in step (220) and then measures the RF impedance (286) of the tissue in step (222). A terminal preparation impedance, such as 1,500 ohms, generally indicates an end to preparation region of a seal model discussed below (see FIG. 16). In the event that the measured RF impedance (286) is less than the predetermined preparation impedance in a step (224), the ultrasonic and RF energies continue to be applied to the tissue with the high upper voltage limit of 100 volts until the continuously measured RF impedance (286) is greater than or equal to the terminal preparation impedance of 1,500 ohms. However, once the measured RF impedance (286) is greater than or equal to the terminal preparation impedance in step (224), controller (46) sets a low upper voltage limit, such as 50 volts, on the RF energy applied to the tissue in a step (226). In response to the low upper voltage limit of 50 volts, controller (46) directs a decrease of RF power (282) in a step (228) and decrease of ultrasonic drive current (280) to apply a lower, terminal ultrasonic power (282) to the tissue in a step (230). In one example, controller (46) may direct another decrease of ultrasonic drive current (280) based a period of time and/or another, higher terminal preparation impedance, such as in the event that the measured RF impedance is inaccurate and/or imprecise due to a bloody field or inadvertent contact with tissue. It should also be understood that ultrasonic power may be decreased in a step-down fashion and/or the ultrasonic power duration may be capped in instances where the impedance measurements are corrupted by a bloody field, inadvertent contact with tissue, etc.

Controller (46) continues measuring RF impedance (286) of the tissue in a step (232) and further compares the measured RF impedance (286) of the tissue from step (232) to a maximum RF impedance, such as 3,000 ohms, in step (234). Generally, once the measured RF impedance (286) is verified as greater than or equal to the maximum RF impedance in step (234), the tissue is effectively sealed in a step (236) while inhibiting transection of the tissue. In practice, the ultrasonic and RF energies are being applied to the tissue over time so that the measured RF impedance (286) increases toward the maximum RF impedance in step (234) and, should too much time pass from the initial time, $T_o$, the method (212) expedites the process to step (234) with an increase in the voltage cap to a surge voltage limit.

To this end, in the event that the measured RF impedance (286) is less than the maximum RF impedance in step (234), controller (46) verifies whether or not the lower voltage limit has been increased to the surge voltage limit in a step (238). If the voltage cap has already been increased to the surge voltage limit as discussed below, then step (232), step (234), and step (238) continually loop until the tissue is sealed in step (236). However, if step (238) verifies that the voltage cap has not already been increased to the surge voltage cap, controller (46) calculates the time from the initial time, $T_o$, in a step (240). Based on the calculated time from $T_o$, a step (242) either directs controller (46) to return to step (232) for further measurement of RF impedance (286) if the calculated time is less than a predetermined termination time or, if the calculated time is greater than or equal to the predetermined termination time, increases the voltage cap to the surge volt limit in a step (244). In either case, measurements of RF impedance (286) are then taken in step (232) and compared against the maximum RF impedance until the tissue is sealed while inhibiting transection of the tissue in step (236). Once the tissue is sealed, controller (46) directs generator (14) to terminate the RF and ultrasonic energies in a step (246).

B. Operation of Surgical System with Tissue Size Determination

Figure 7:
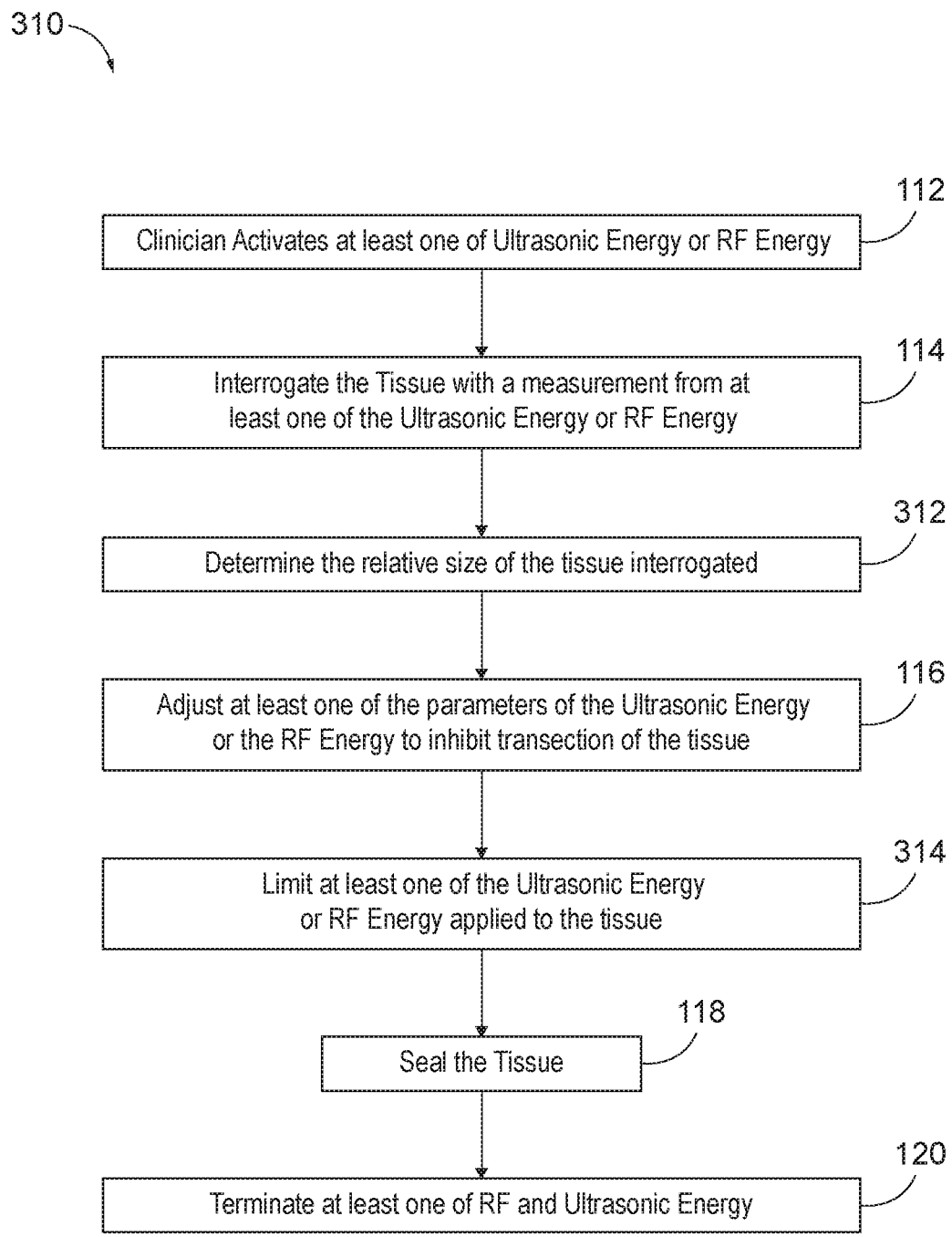
FIG. 7 depicts a flowchart of a high-level method of interrogating and sealing the tissue based on the method of FIG. 3 in conjunction with determining a relative size of the tissue with the ultrasonic surgical instrument.

FIG. 7 illustrates a high-level method (310) of interrogating a sealing tissue similar to the high-level method (110) discussed above for interrogating and sealing tissue with respect to FIG. 3. More particularly, high-level method (310) includes steps (112, 114, 116, 118, and 120) for activation, interrogation, parameter adjustment, tissue sealing, and termination. In addition, high-level method (310) includes a step (312) of determining a relative size of the tissue interrogated after step (114) as well as a step (314) of limiting at least one of the ultrasonic and RF energies applied to the tissue after step (116).

As discussed above, various steps may be performed alone, in combination, or exchanged with like steps. By way of further example, as applicable to high-level method (310). Tissue size determination of step (312) and energy limit step (314) represent a high-level method steps with more particular versions thereof being capable of being performed alone, in combination, or exchanged with one another. The invention is thus not intended to be unnecessarily limited to a specific version of tissue size determination step (312) or energy limit step (314) with any particular interrogation step (114) and/or parameter adjustment step (116).

Figure 8A:
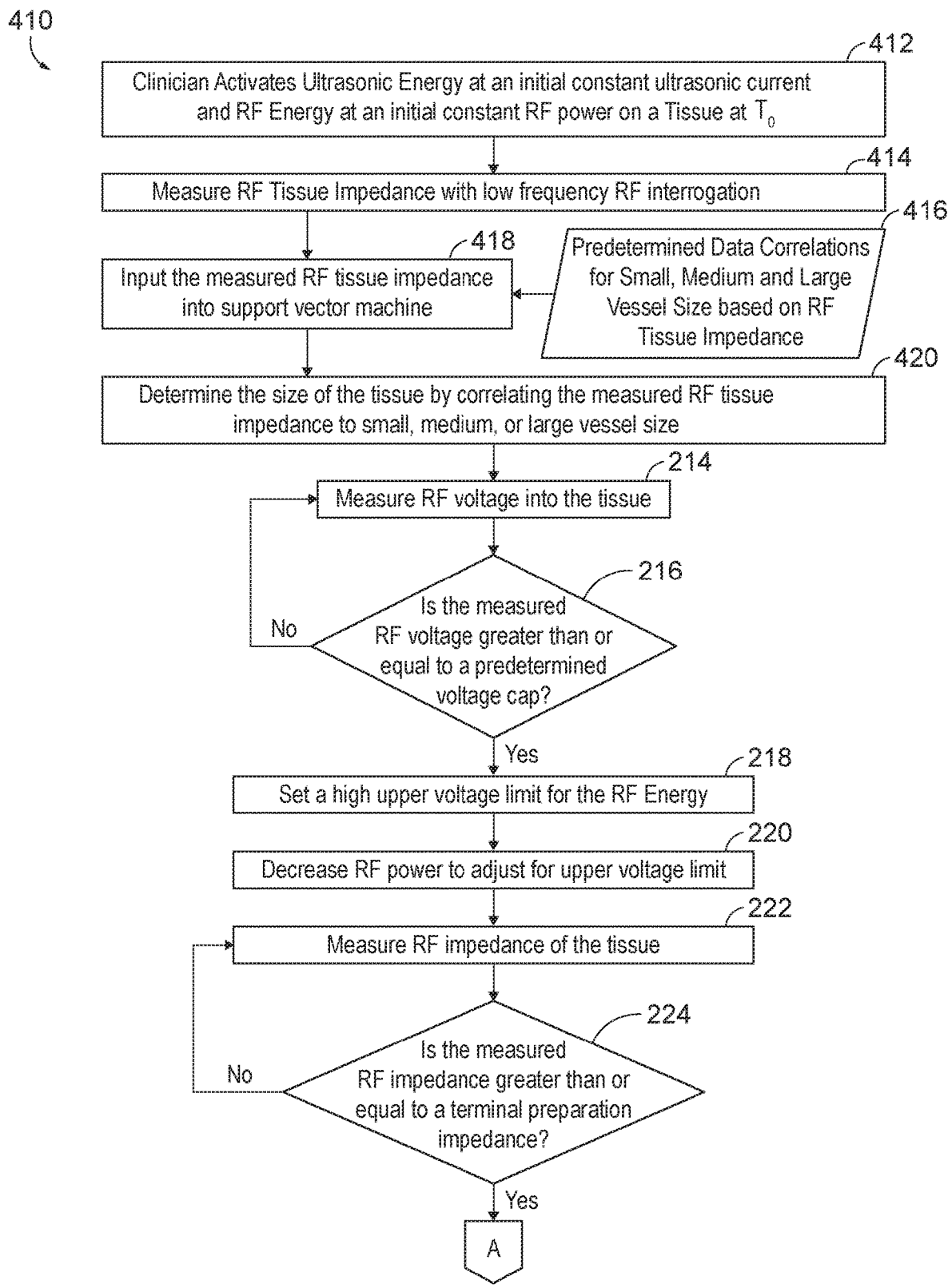
FIGS. 8A-8B depict a flowchart of a second exemplary version of implementing the method of FIG. 7 with a first tissue size determination and set voltage limits based on RF impedance.
Figure 8B:
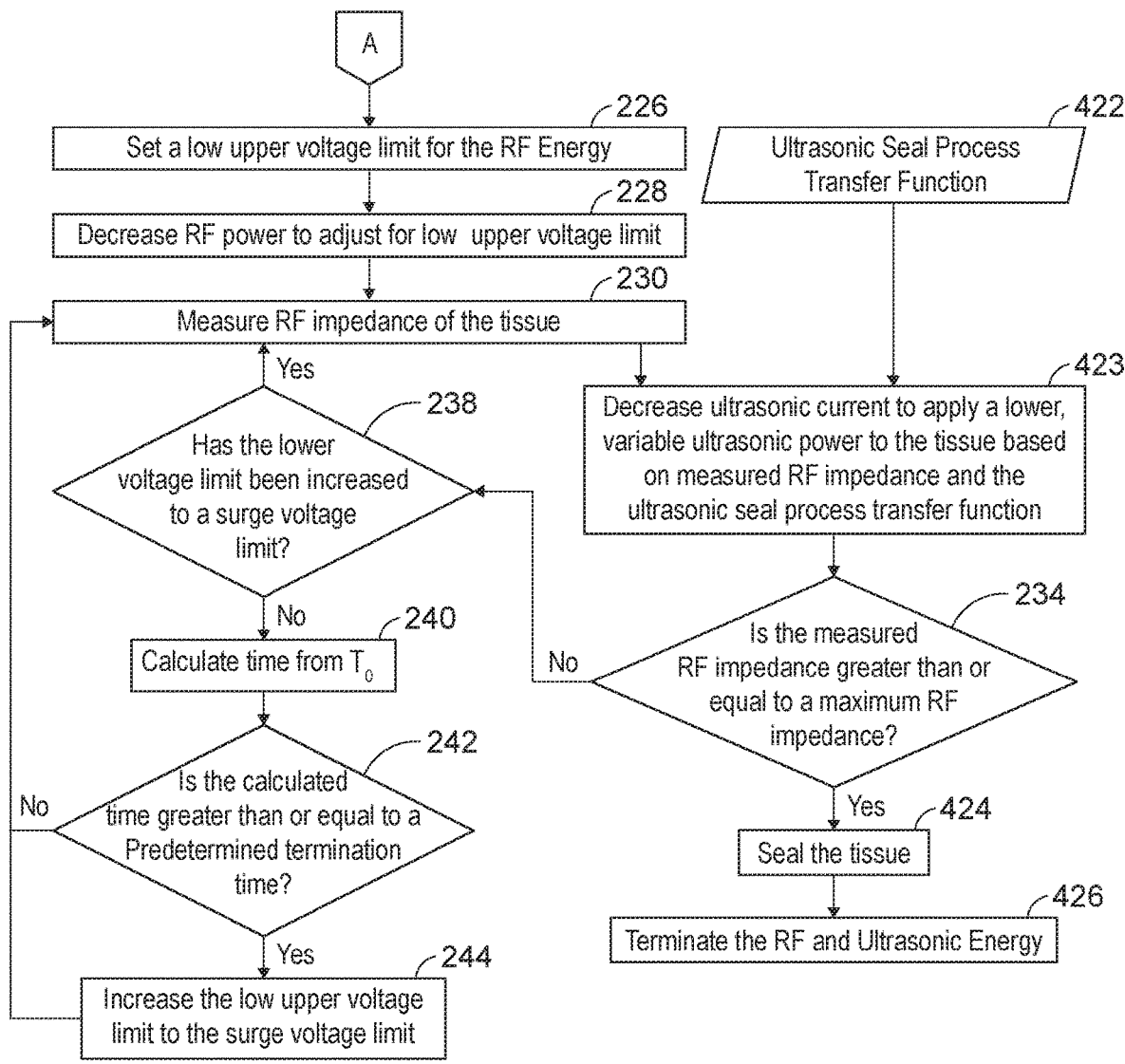
Figure 9:
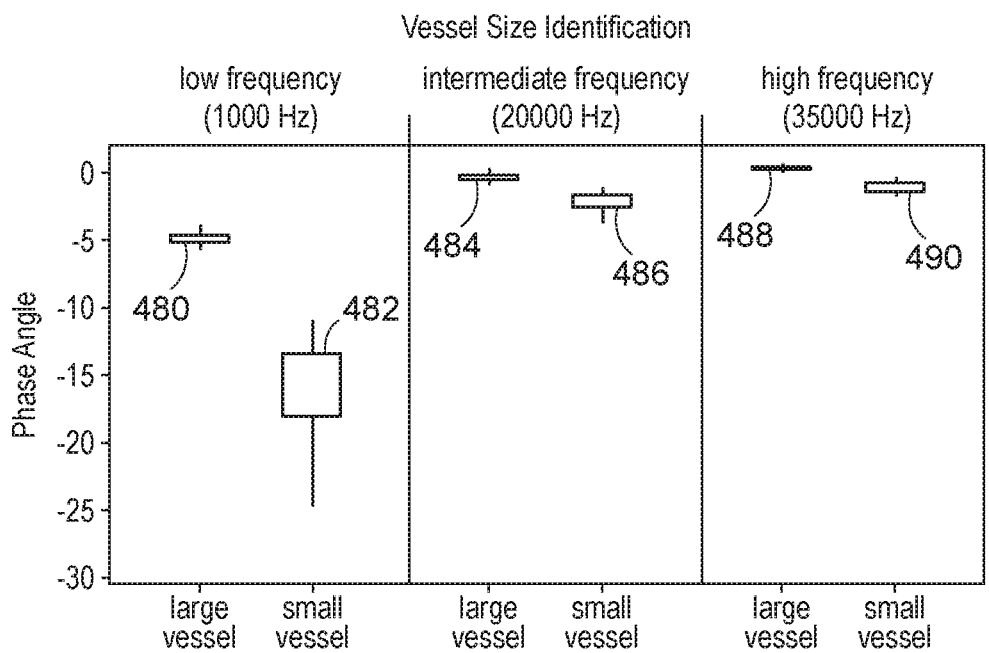
FIG. 9 depicts a graph of vessel size data based on a phase angle differential for various energy frequencies.

Various tissue sizes described herein are referred to relatively as a small vessel size, a medium vessel size, and a large vessel size. By way of example, a small vessel size is less than approximately 4 mm diameter, such as a thyrocervical artery, a medium vessel size is approximately 4 mm to approximately 6 mm diameter vessel, such as carotid artery, and a large vessel size is approximately 6 mm to approximately 7 mm diameter vessel, such as a carotid bundle. The terms "small," "medium," and "large" with respect to vessel sizes, which may also be referred to generally as tissue sizes, are relative to each other and not intended to unnecessarily limit the invention described herein.

i. Second Exemplary Version of Interrogating and Sealing Tissue with a First Tissue Size Determination and Set Voltage Limits Based on RF Impedance A second exemplary version for a method (410) of interrogating and sealing tissue with operating surgical system (10) of FIG. 1 is illustrated in FIGS. 8A-8B. The clinician actives ultrasonic and RF energies respectively at an initial ultrasonic power with a constant ultrasonic drive current and an initial constant RF power on tissue at an initial time, $T_o$, in accordance with a step (412). Controller (46) then measures RF impedance, specifically a complex RF impedance, with a relatively low frequency RF interrogation signal, such as 1000 Hz, in a step (414). Notably, with respect to FIG. 9, relatively low frequency RF interrogation signals provide for measurements of complex RF impedance with a magnitude and a greater phase angle differential between large and small tissues than intermediate and high frequency RF interrogations signals, such as 2,000 Hz and 35,000 Hz, respectively. For example, the phase angle differential for low frequency interrogation of large vessels (480) and small vessels (482) is relatively large and distinguishable. In contrast, the phase angle differential of intermediate frequency interrogation for large vessels (484) and small vessels (486) as well as the phase angle differential of high frequency interrogation for large vessels (488) and small vessels (490) relatively small and less distinguishable. Predetermined data of such differentials are stored for access by controller (46) that correlate to small, medium, and large vessel sizes based on RF tissue impedance measurement data (416).

With respect to a step (418), the measured RF tissue impedance from step (414) and the predetermined data correlations (416) are input into a classifier, such as a support vector machine, which thereby completes a step (420) of determining the size of the tissue based on the predetermined data correlations (416). The support vector machine of the present example is trained based on a variety of ex vivo and/or in vivo tissue sizes for use in step (420). Once the relative tissue size has been determined, the vessel size is stored by controller (46) in step (420) further later use. Measurements of RF voltage and voltage limit settings are then performed as discussed above with respect to step (214) through step (228) until controller measures RF impedance of the tissue in step (230). While the present example includes the support vector machine for completing one or more steps, other classifiers, such as a neural network, a recurrent neural network, a Bayesian belief network, k-means, fuzzy classifiers, and/or a decision tree may also be used. Such other classifiers may also be used in any of the following references to the support vector machine below. The invention is thus not intended to be unnecessarily limited to the support vector machine.

Figure 10:
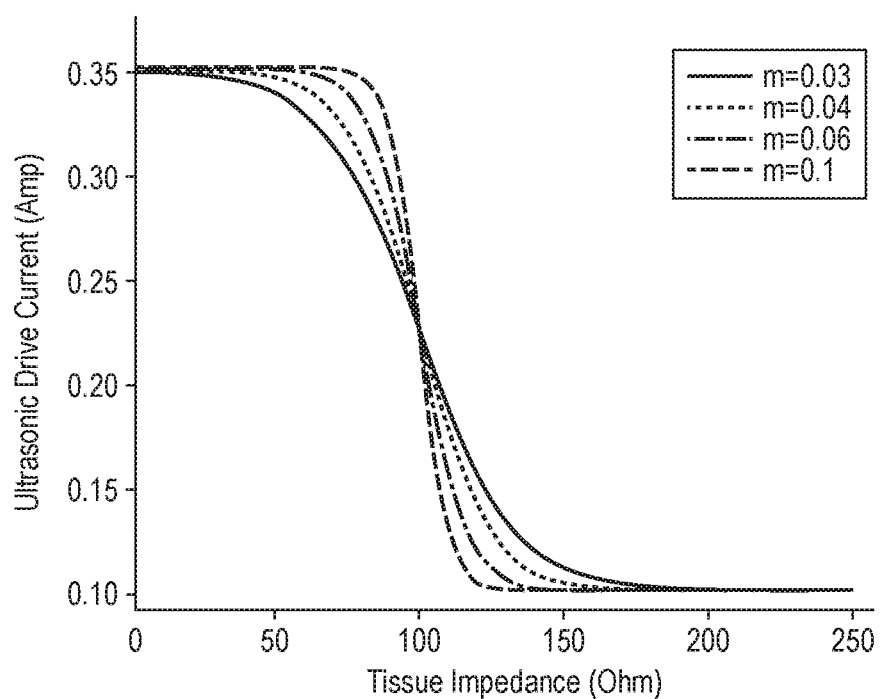
FIG. 10 depicts a graph of a variable ultrasonic energy based on an exemplary ultrasonic seal process transfer function.

Controller (46) accesses a stored ultrasonic seal process transfer function (422), the stored vessel size of the tissue from step (420), and the measured RF impedance of the tissue from step (230) for decreasing the ultrasonic powering current of the ultrasonic energy in a step (423). Rather than constant ultrasonic powering current delivered at relatively higher or lower values, ultrasonic seal process transfer function is configured to variably decreasing ultrasonic powering current with similarly variable ultrasonic power to inhibit transecting the tissue of the determined vessel size. With respect to FIG. 10, one example of ultrasonic seal process transfer function (422) is represented below as Equation 1 with the following parameters: $I_h$ is an applied ultrasonic power; $I_{hmin}$ is a lower post-preparation ultrasonic power; $I_{hmax}$ is a higher preparation ultrasonic power; m is a rate of decay of ultrasonic power based on measured tissue impedance; $Z_{transition}$ is an RF impedance with ultrasonic power at 50% of an ultrasonic power range; and Z is measured tissue impedance. One or more of these parameters are optimized for small, intermediate, and large vessels to encourage sealing of the tissue without transecting the tissue. FIG. 10 illustrates various examples where values from m are different based on RF impedance of the tissue and $I_{hmin}$=0.1 amps, $I_{hmax}$=0.35 amps, and $Z_{transition}$=100 ohms.

Ultrasonic Seal Process Transfer Function $$I_h = \left(\frac{I_{hmin} - I_{hmax}}{2}\right) \cdot (\tanh(m \cdot Z - m \cdot Z_{transition}) - 1) + I_{hmin} \quad \text{Equation 1}$$

Figure 11:
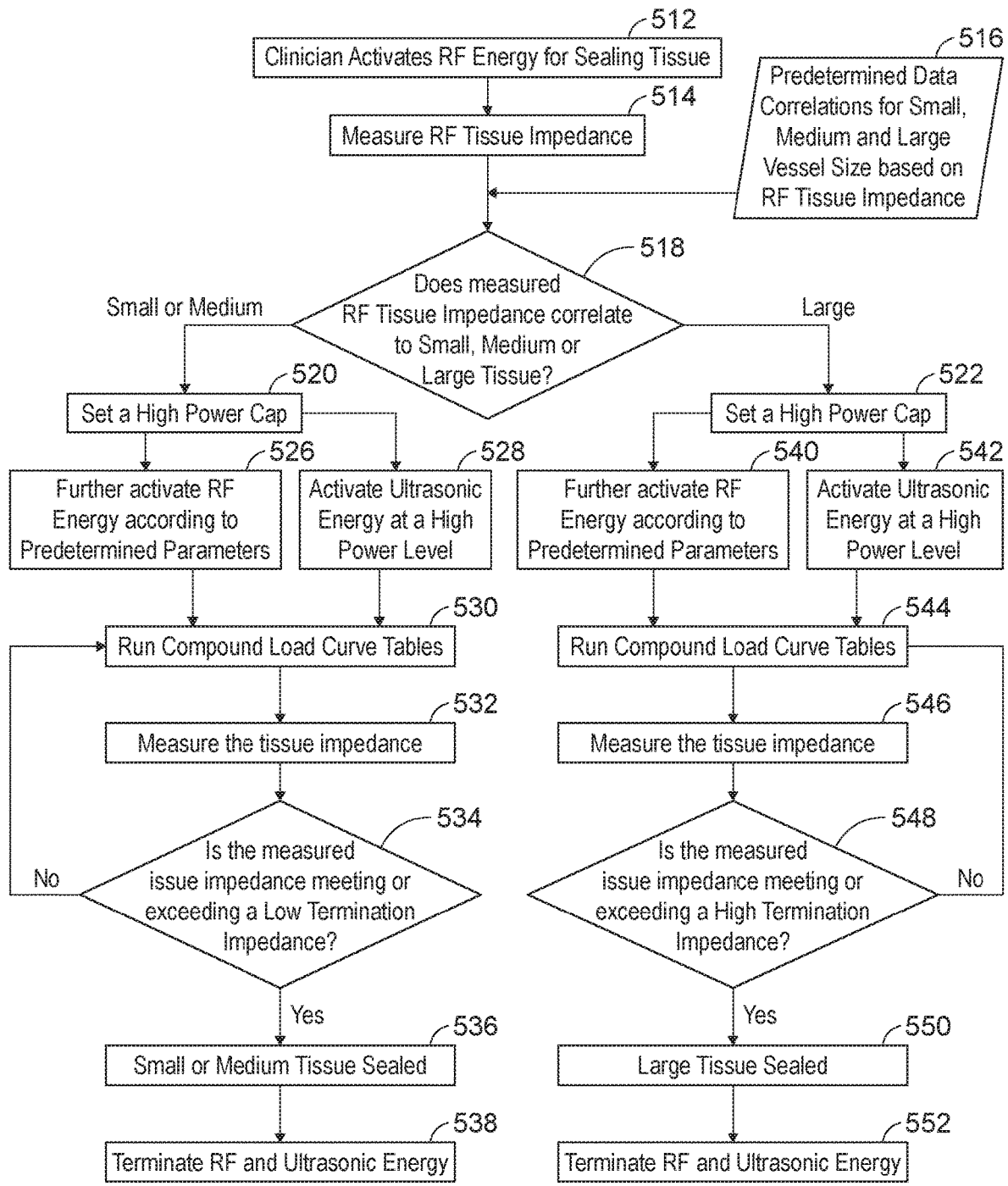
FIG. 11 depicts a flowchart of a third exemplary version of implementing the method of FIG. 7 with a second tissue size determination and RF impedance termination.

In any case, with respect to FIG. 8B, ultrasonic powering current of ultrasonic power decreases in step (423) and method (410) continues by verifying time from the initial time, $T_o$, and increasing the low upper voltage limit to the surge voltage limit as discussed above with respect to step (238) through step (244), which is followed by further measurement of RF impedance in step (232). Such steps continually loop until the measured RF impedance is greater than or equal to the maximum RF impedance in step (234), at which the tissue is sealed while inhibiting transection thereof in a step (424). Once the tissue is sealed, controller (46) directs generator (14) to terminate the RF and ultrasonic energies in a step (426).

ii. Third Exemplary Version of Interrogating and Sealing Tissue with a Second Tissue Size Determination and RF Impedance Termination FIG. 11 illustrates a third exemplary version for a method (510) of interrogating and sealing tissue with operating surgical system (10) of FIG. 1. The clinician activates RF energy on tissue in accordance with a step (512). Controller (46) then interrogates the tissue with measurements of RF impedance of the tissue in a step (514). Predetermined data of RF impedance values are stored for access by controller (46) that correlate to small, medium, and large vessel sizes based on RF tissue impedance measurement data (516). In a step (518), controller (46) compares the measured RF impedance of the tissue to the predetermined data correlations and determines whether the tissue size is small, medium, or large. In the event that the tissue is the small or medium vessel size, method (510) continues to a step (520) for use in a low termination impedance process. However, in the event that the tissue is the large vessel size, method (510) continues to a step (522) for use in a high termination impedance process. The following will address these low and high termination impedance processes in turn. Notably, ultrasonic energy may also be activated in step (512) in some examples, but, in the present example, RF energy activation simply interrogates the tissue rather than applying sufficient energy for therapeutic treatment of the tissue.

With respect to the low termination impedance process, controller (46) sets a high power cap for ultrasonic and RF power in step (520). One example high power cap is 200 watts. Following setting of the high power cap, RF energy is further activated according to predetermined RF energy parameters in a step (526) for the determined tissue size, and ultrasonic energy is activated at a high power level in a step (528) for the determined tissue size. Controller (46) accesses and runs compound load curve tables for the determined tissue size in a step (530) simultaneously with ultrasonic and RF energy activation and then measures the tissue impedance again in a step (532). The controller (46) then compares the measured tissue impedance from step (532) to the low termination impedance and determines whether the measured tissue impedance is greater than or equal to the lower termination impedance in a step (534). One exemplary low termination impedance is 1,000 ohms.

If the measured tissue impedance is less than the low termination impedance in step (534), method (510) loops back to run compound load curves and again measure the tissue impedance in respective step (530) and step (532) for another comparison in step (534). Once the measured tissue impedance is greater than or equal to the low termination impedance, the small or medium vessel is effectively sealed in a step (536) while inhibiting transection of the tissue. Following the tissue seal in step (536), controller (46) terminates the RF and ultrasonic energies in a step (538) for completion of the low termination impedance process.

Figure 12:
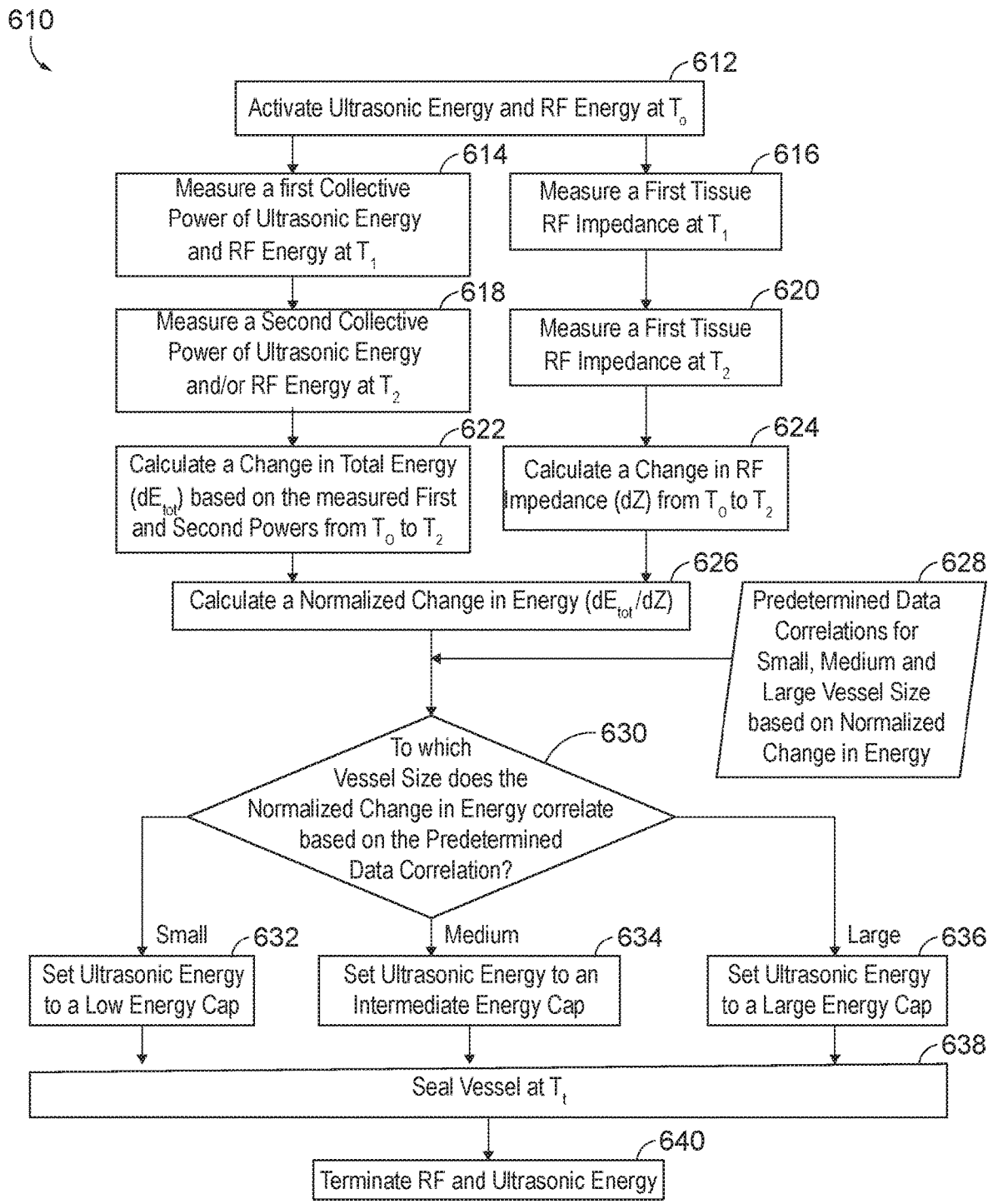
FIG. 12 depicts a flowchart of a fourth exemplary version of implementing the method of FIG. 7 with a third tissue size determination and ultrasonic energy caps based on a normalized energy change.

With respect to the high termination impedance process, controller (46) sets a high power cap for ultrasonic and RF energies in step (522). Alternatively, controller (46) may set a high power cap for only RF energy or only ultrasonic energy in step (522). The particular high power cap may thus be configured based on the tissue size determination and may similarly apply for the lower termination process discussed above in greater detail. Following setting of the high power cap, RF energy is further activated according to predetermined RF energy parameters in a step (540) for the determined tissue size, and ultrasonic energy is activated at a high power level in a step (542) for the determined tissue size. Controller (46) then accesses and runs compound load curve tables for the determined tissue size in a step (544) and measures the tissue impedance again in a step (546). The controller (46) then compares the measured tissue impedance from step (546) to the high termination impedance and determines whether the measured tissue impedance is greater than or equal to the high termination impedance in a step (548). One example high termination impedance is 2,000 ohms. If the measured tissue impedance is less than the low termination impedance in step (548), method (510) loops back to run compound load curves and again measure the tissue impedance in respective step (544) and step (546) for another comparison in step (548). Once the measured tissue impedance is greater than or equal to the low termination impedance, the large vessel is effectively sealed in a step (550) while inhibiting transection of the tissue. Following the tissue seal in step (550), controller (46) terminates the RF and ultrasonic energies in a step (552).

iii. Fourth Exemplary Version of Interrogating and Sealing Tissue with a Third Tissue Size Determination and Ultrasonic Energy Caps Based on Normalized Energy Change FIG. 12 illustrates a fourth exemplary version for a method (610) of interrogating and sealing tissue with operating surgical system (10) of FIG. 1. The clinician activates RF and ultrasonic energies on tissue in accordance with a step (612) at an initial time, $T_o$. Controller (46) then interrogates the tissue with measurements of a first collective power of RF and ultrasonic energies applied to the tissue at time, $T_1$, following the initial time, $T_o$, in a step (614). Simultaneously, at time $T_1$, controller (46) interrogates the tissue with a measurement of an RF impedance of the tissue in a step (616). Following measurements in step (614) and step (616), a second collective power of ultrasonic and RF energies applied to the tissue and another measurement of tissue impedance is performed respectively in a step (620) and a step (622) simultaneously at another time, $T_2$. While successive times $T_1$ and $T_2$ may vary from $T_o$, in the present example, $T_1$ and $T_2$ are generally less than approximately 0.5 seconds from the initial time, $T_o$, so as to occur relatively early in method (610) for sealing the tissue.

Measurements of first and second collective power and corresponding RF impedances are respectively stored in step (614), step (618), step (616), and step (620) for use in a step (622) and a step (624) to thereby determine a size of the tissue. To this end, controller (46) calculates a change in total energy, $dE_{tot}$, from $T_o$ to $T_2$ and stores the change in total energy, $dE_{tot}$, in step (622), while also calculating a change in RF impedance, $dZ$, from $T_o$ to $T_2$ and storing the change in total energy, $dZ$, in step (624). Based on $dE_{tot}$ and $dZ$, this change in energy is normalized with the change in RF impedance in order to calculate a normalized change in energy ($dE_{to}/dZ$) in a step (626).

Figure 13:
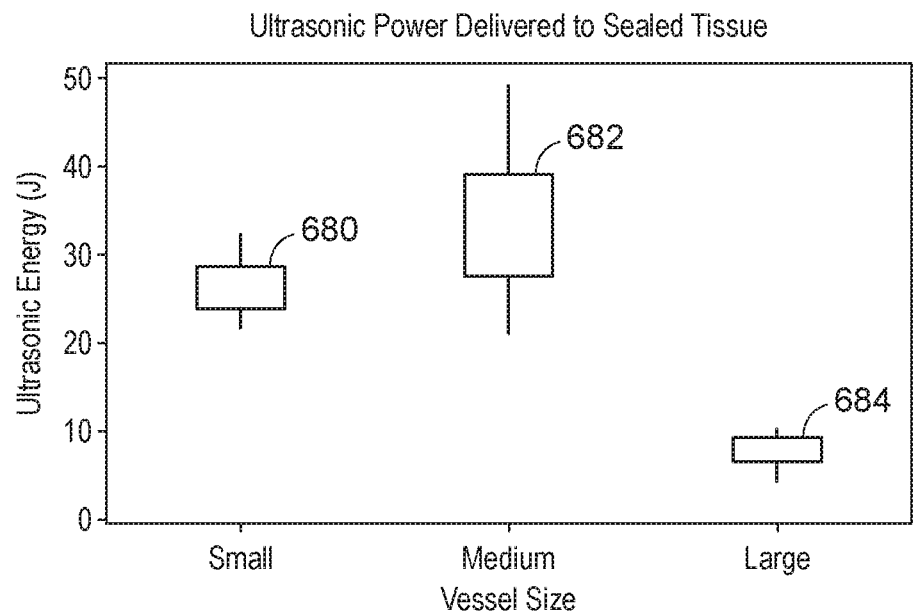
FIG. 13 depicts a graph of ultrasonic power delivery data for various tissue sizes.
Figure 14:
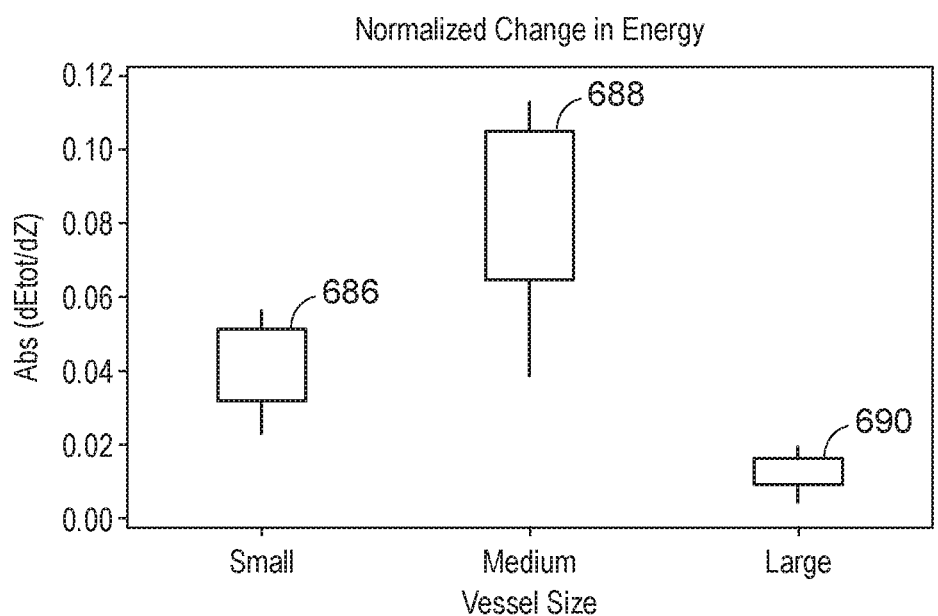
FIG. 14 depicts a graph of vessel size data based on a normalized energy differential.

Generally, a total ultrasonic energy applied to the tissue to at least some extent correlates to sealing particular sizes of tissue while inhibiting transection of the tissue as shown in FIG. 13, shown respectively for small vessels (680), medium vessels (682), and large vessels (684). Going further, normalizing the total change in energy applied to the tissue, $dE_{to}$, with the change in RF impedance applied to tissue, $dZ$, provides for distinguishable absolute values of normalized change in energy ($dE_{to}/dZ$) for respective correlations to small, medium, and large vessels sizes (686, 688, 690) as shown in FIG. 14. Predetermined data correlations (628) of normalized change in energy to small, medium, and large vessel sizes are stored for access by controller (46), which compares predetermined data correlations (628) to the calculated normalized change in energy of step (626) in a step (630) shown in FIG. 12. Step (630) thus determines whether the vessel size is relatively small, medium, or large.

Figure 15:
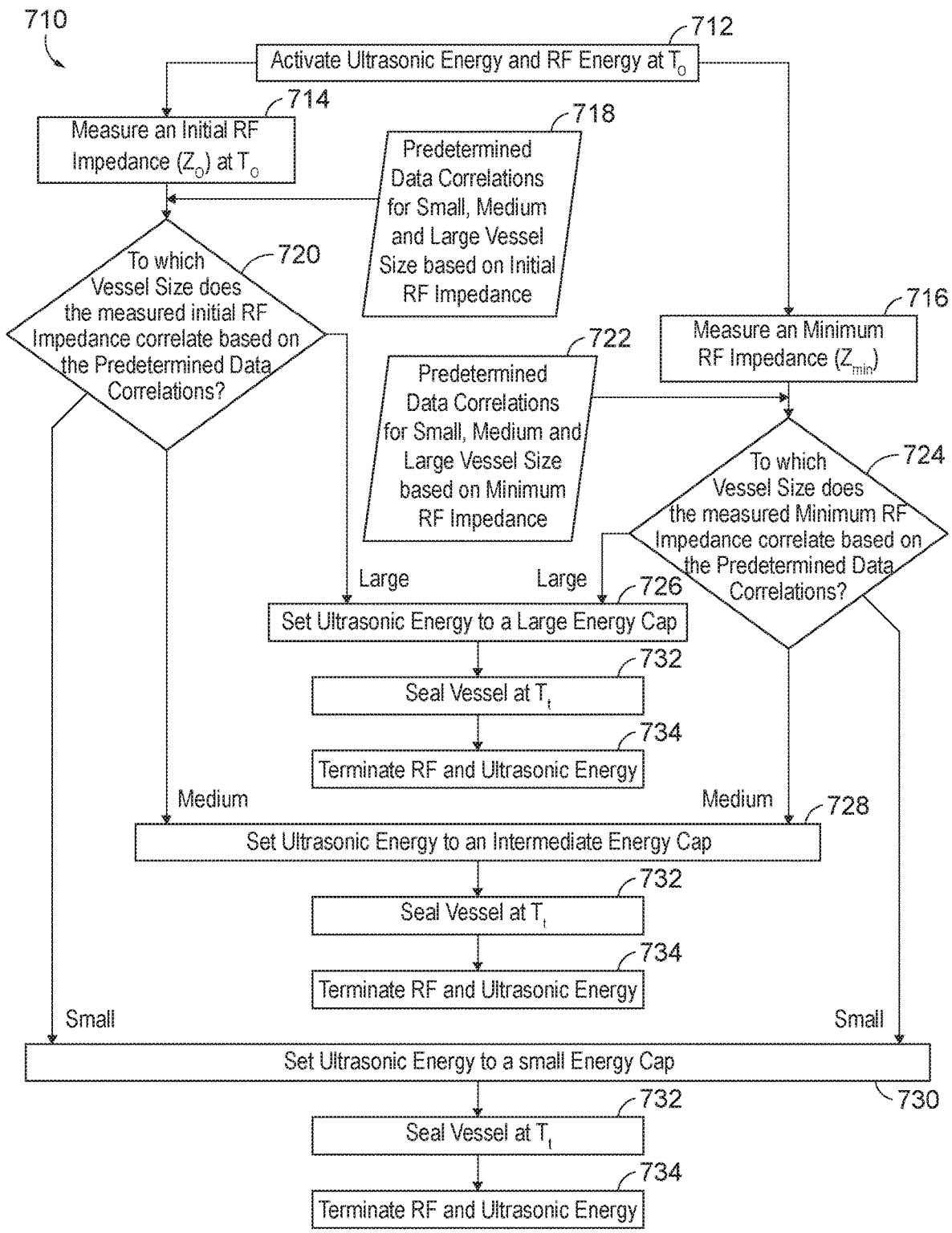
FIG. 15 depicts a flowchart of a fifth exemplary version of implementing the method of FIG. 7 with a fourth tissue size determination and ultrasonic energy caps based on RF impedance.
Figure 16:
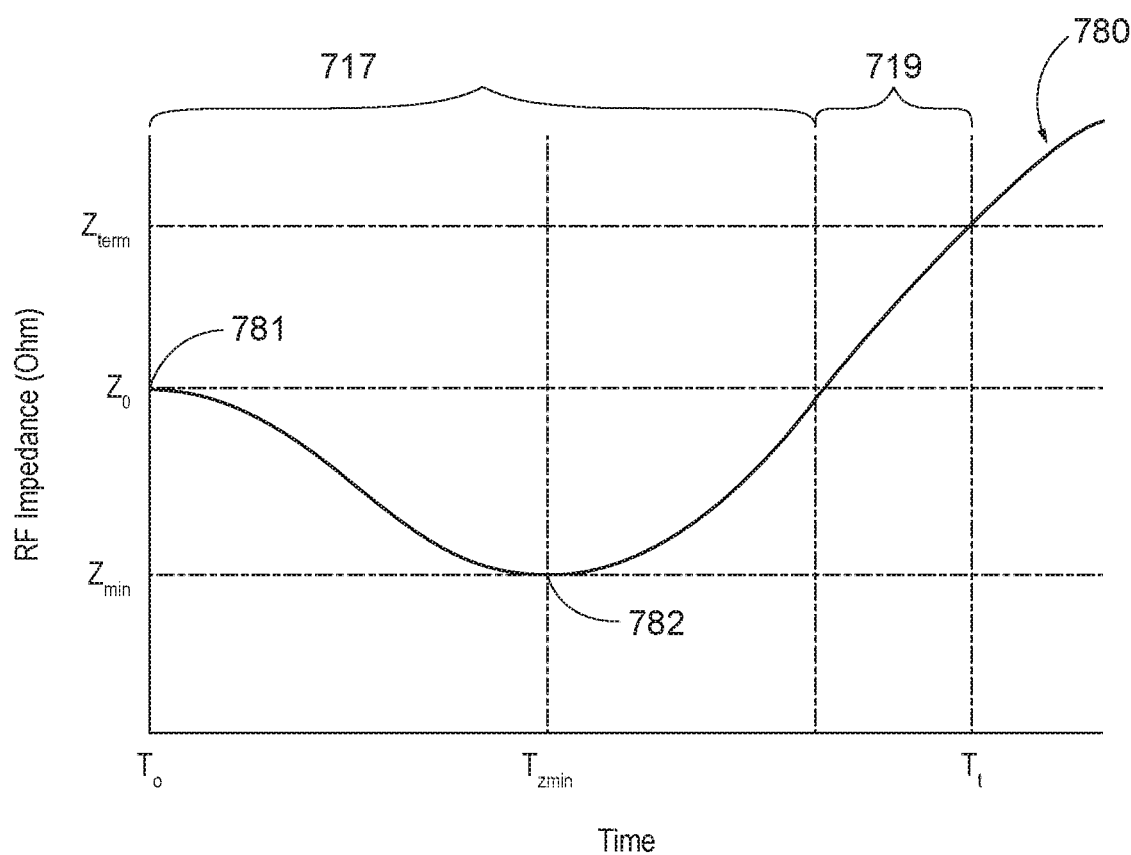
FIG. 16 depicts a graph of tissue RF impedance measurements during the version of FIG. 15.

Based on the determined vessel size from step (630), controller (46) sets ultrasonic energy applied to the tissue to an energy cap configured to seal the vessel, while inhibiting transection of the vessel. In the present example, determining that the tissue is either small, medium or large sets the ultrasonic energy applied to the tissue respectively to a low energy cap in a step (632), an intermediate energy cap (634), or a large energy cap (636). RF energy and the ultrasonic energy continues to be applied until reaching the set energy cap, at which time ultrasonic energy is terminated or reduced such that the vessel is sealed in a step (638) while inhibiting transection of the tissue. Once sealed, controller (46) terminates the application of any remaining RF and ultrasonic energies to the tissue in a step (640).

iv. Fifth Exemplary Version of Interrogating and Sealing Tissue with a Fourth Tissue Size Determination and Ultrasonic Energy Caps Based on RF Impedance FIG. 15 illustrates a fifth exemplary version for a method (710) of interrogating and sealing tissue with operating surgical system (10) of FIG. 1 based on RF impedance, exemplary measurements (780) of which are shown in FIG. 16. The clinician activates RF and ultrasonic energies on tissue in accordance with a step (712) at an initial time, $T_o$. Controller (46) also simultaneously interrogates the tissue with measurements of an initial RF impedance (781), $Z_o$, of the tissue at the initial time, $T_o$, in a step (714) and stores the initial RF impedance (781), $Z_o$, for one determination of vessel size discussed below in more detail. In addition, controller (46) continues to interrogate the tissue with additional RF impedance measurements (780) in a step (716). During these repeated RF impedance measurements (780), step (716) identifies the minimum RF impedance (782), $Z_{min}$, of the tissue at a time, $T_{zmin}$, which is identified in one example of collected RF impedance measurements (780) in FIG. 16 Generally, RF impedance measurements (780) of tissue follow the seal model shown in FIG. 16, such that, in one example, the slope of the function representative of the RF impedance data is zero between the decreasing and increasing RF impedance. In the present example, a preparation region of the seal model, as indicated by reference numeral (717) decreases from the time, $T_o$, until remaining relatively constant followed by increasing RF impedance to a seal region, as indicated by reference numeral (719). This zero slope in preparation region (717) indicates the time, $T_{min}$, of the minimum RF impedance (782), $Z_{min}$, which is stored for use in another determination of vessel size discussed below in more detail. The following thus describes method (760) with two distinct determinations of tissue size based respective on initial tissue impedance (781), $Z_o$, and minimum tissue impedance (782), $Z_{min}$, that may be processed, as described in the present example, in parallel with each other.

With respect to initial RF impedance (781), $Z_o$, of the tissue, controller (46) accesses stored predetermined data correlations (718), which, based on prior data, correlate initial RF impedance measurement data to small, medium, or large vessels. A step (720) compares the measured initial RF impedance (781), $Z_o$, to the predetermined data correlations (718) and determines whether then vessel is small, medium, or large. Similarly, with respect to minimum RF impedance (782), $Z_{min}$, controller (46) accesses stored predetermined data correlations (722), which, based on prior data, correlate minimum RF impedance measurement data to small, medium, or large vessels. A step (724) compares the measured minimum RF impedance (782), $Z_{min}$, to the predetermined data correlations (722) and determines whether then vessel is small, medium, or large.

FIG. 15 and Table 4 represent one exemplary logic applied by controller (46) when step (720) or step (274) determine the size of the vessel being treated for sealing the tissue while inhibiting transection of the tissue applied in each of step (726), step (728), and step (730). In the event that either the initial RF impedance (781), $Z_o$, is between approximately 0 ohms and approximately 160 ohms, or the minimum RF impedance (782), $Z_{min}$, is between approximately 0 ohms and approximately 48 ohms, then the ultrasonic energy cap is set to a large energy cap, such as approximately 50 joules, in step (726). In the event that either the initial RF impedance (781), $Z_o$, is between approximately 160 ohms and approximately 225 ohms, or the minimum RF impedance (782), $Z_{min}$, is between approximately 48 ohms and approximately 90 ohms, then the ultrasonic energy cap is set to an intermediate energy cap, such as approximately 32 joules, in step (728). In the event that either the initial RF impedance (781), $Z_o$, is greater than approximately 225 ohms, or the minimum RF impedance (782), $Z_{min}$, is greater than approximately 90 ohms, then the ultrasonic energy cap is set to a small energy cap, such as approximately 10 joules, in step (730).

While the present example applies "or" logic for determining and setting large, intermediate, and small energy caps, other examples may apply one or more "and" logic for setting energy caps in one or more of the small, medium, or large sizes. Similarly, one or more other examples may use differing values and/or ranges of values for determining such energy outputs, which may also vary depending on tissue and use. The invention is thus not intended to be unnecessarily limited to the logic and values described herein. It will be further appreciated that in alternative embodiments, RF energy may also be similarly limited, such that the invention is not intended to be unnecessarily limited to only ultrasonic energy caps as shown in the present example. Furthermore, in the event that multiple RF impedance conditions occur in the present example, controller (46) selects the higher of the ultrasonic energy caps available to the multiple RF impedance conditions.

TABLE 4

Energy Cap Setting Logic

| | Input for Vessel Size Determination | | | Energy |
|---|---|---|---|---|
| Vessel Size | Initial RF Impedance $Z_o$ (Ohms) | Logic Statement | Minimum RF Impedance $Z_{min}$ (Ohms) | Output Ultrasonic Energy Cap (J) |
| Large | 0-160 | or | 0-48 | 50 |
| Medium | 160-225 | or | 48-90 | 32 |
| Small | >225 | or | >90 | 10 |

Figure 17:
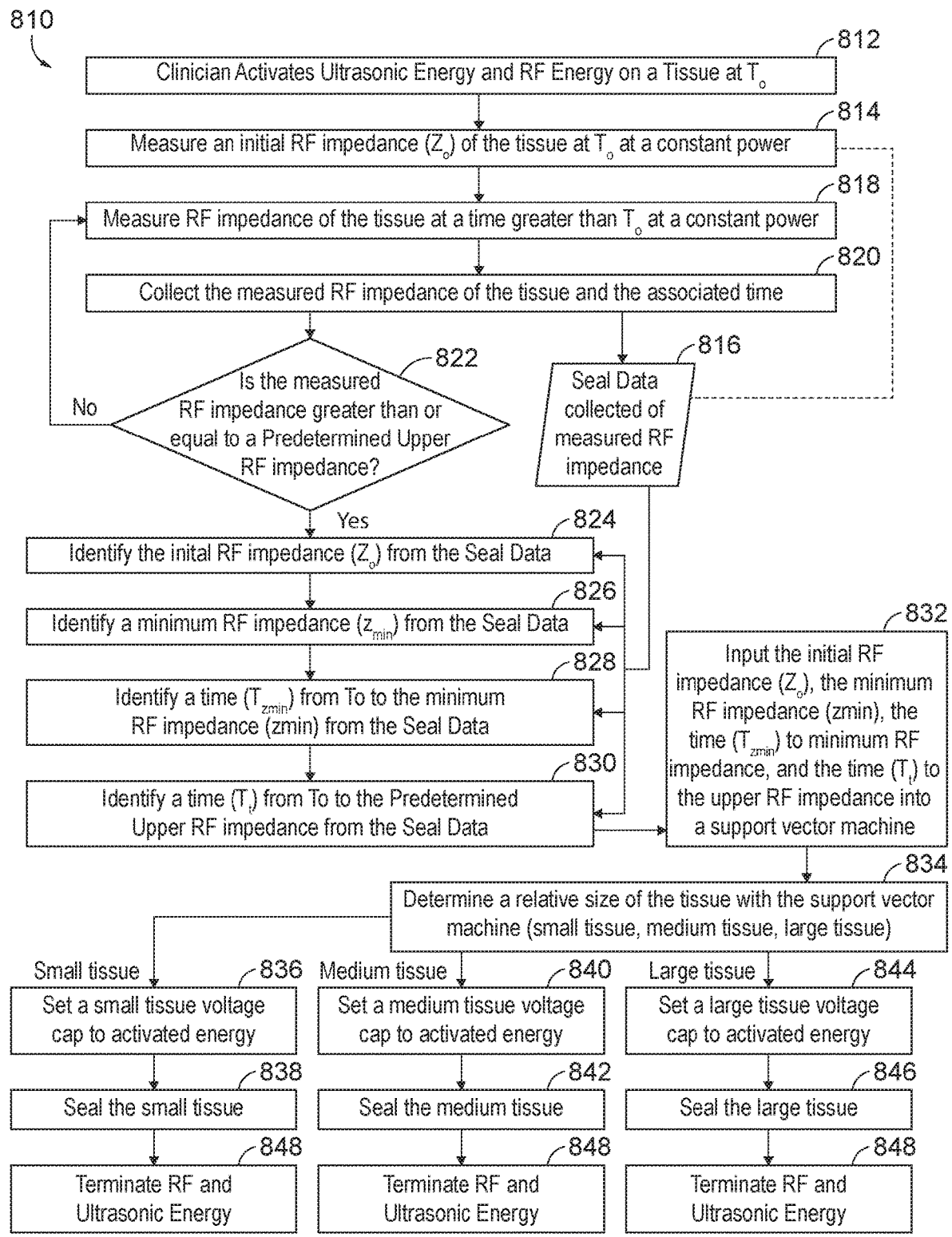
FIG. 17 depicts a flowchart of a sixth exemplary version of implementing the method of FIG. 7 with a fifth tissue size determination and voltage caps based on RF impedance data.

Following setting of the ultrasonic energy cap in one of step (726), step (728), or step (730), the vessel is sealed while inhibiting transection of the tissue in a step (732) at a termination time, $T_t$. Once tissue is sealed in step (732), controller (46) directs ultrasonic and RF energies to terminate in a step (734).

v. Sixth Exemplary Version of Interrogating and Sealing Tissue with a Fifth Tissue Size Determination and Voltage Caps Based on RF Impedance Data FIG. 17 illustrates a sixth exemplary version for a method (810) of interrogating and sealing tissue with operating surgical system (10) of FIG. 1. The clinician activates RF and ultrasonic energies on tissue in accordance with a step (812) at an initial time, $T_o$. Controller (46) also simultaneously interrogates the tissue with measurements of an initial RF impedance, $Z_o$, of the tissue at the initial time, $T_o$, in a step (814) and stores the initial RF impedance, $Z_o$ in an RF impedance data set (816) for later use. In addition, controller (46) continues to interrogate the tissue with additional RF impedance measurements in a step (818) as time passes beyond the initial time, $T_o$. Once the RF impedance measurement after the initial time, $T_o$, is collected in a step (820), such RF impedance is simultaneously stored in the RF impedance data set (816) and compared against a predetermined upper RF impedance in a step (822). The comparison of measured RF impedance to the predetermined upper RF impedance in step (822) is generally configured to collect a series of RF impedance measurements of the tissue through approximately an entirety of the seal model (see FIG. 16). Thus, in the event that the measured RF impedance is less than the predetermined upper RF impedance in step (822), the RF impedance measurement, collection, storage, and comparison of step (818), step (820), and step (822) continuously loop until the RF impedance measurement of step (818) is greater than or equal to the predetermined upper RF impedance. Once the measured RF impedance is greater than or equal to the predetermined upper RF impedance in step (822), the preparation region (717) (see FIG. 16) of the therapeutic effect on the tissue is complete such that a complete set of measurements can be identified and analyzed for determining the size of the tissue. In the present example, the above measurements are taken with an application of 20 watts of constant power in the seal model, which ends in the present model when the RF impedance increases to 1,500 ohms.

From the comparison of step (822), controller (46) next identifies the initial RF impedance, $Z_o$, from the RF impedance data set (816) in a step (824) and then a minimum RF impedance, $Z_{min}$, from the RF impedance data set (816) in a step (826). Controller (46) then further identifies a time, $T_{zmin}$, from the initial time, $T_o$, to the minimum RF impedance, $Z_{min}$, from the RF impedance data set (816) in a step (828) as well as a time, $T_f$, from the initial time, $T_o$, to the predetermined upper RF impedance from the RF impedance data set (816) in a step (830). Each of the initial RF impedance, $Z_o$, the minimum RF impedance, $Z_{min}$, the time, $T_{zmin}$, to the minimum RF impedance, and the time, $T_f$, to the upper RF impedance is input into a classifier, such as a support vector machine, in a step (832). In addition, the preparation time, which is defined in one example as a time for tissue impedance to increase to 1,500 ohm under a constant power delivery of 20 watts, may also be input into the support vector machine in step (832). Based on prior sets of RF impedance data correlated to tissue size, support vector machine thus determines the relative size of the tissue as small, medium or large in a step (834).

Alternatively or in addition to the prior sets of RF impedance data, other input data, such as acoustic measurements, may be used for adjusting criteria for tissue size classification with a general mathematical classification. While the description of tissue size classification contained herein includes discrete classifications of small, medium, and large, such classification may also be an analog continuum of tissue size rather than discrete classification. Such tissue size classification is generally correlated to electrical behavior, such as RF impedance as described above. To this end, method (810), as well as other methods described herein with tissue size classification, may simply proceed based on this electrical behavior rather than the correlation to tissue size. The invention is thus not intended to be unnecessarily limited to discrete tissue size classification nor unnecessarily rely upon tissue size classification.

Figure 18:
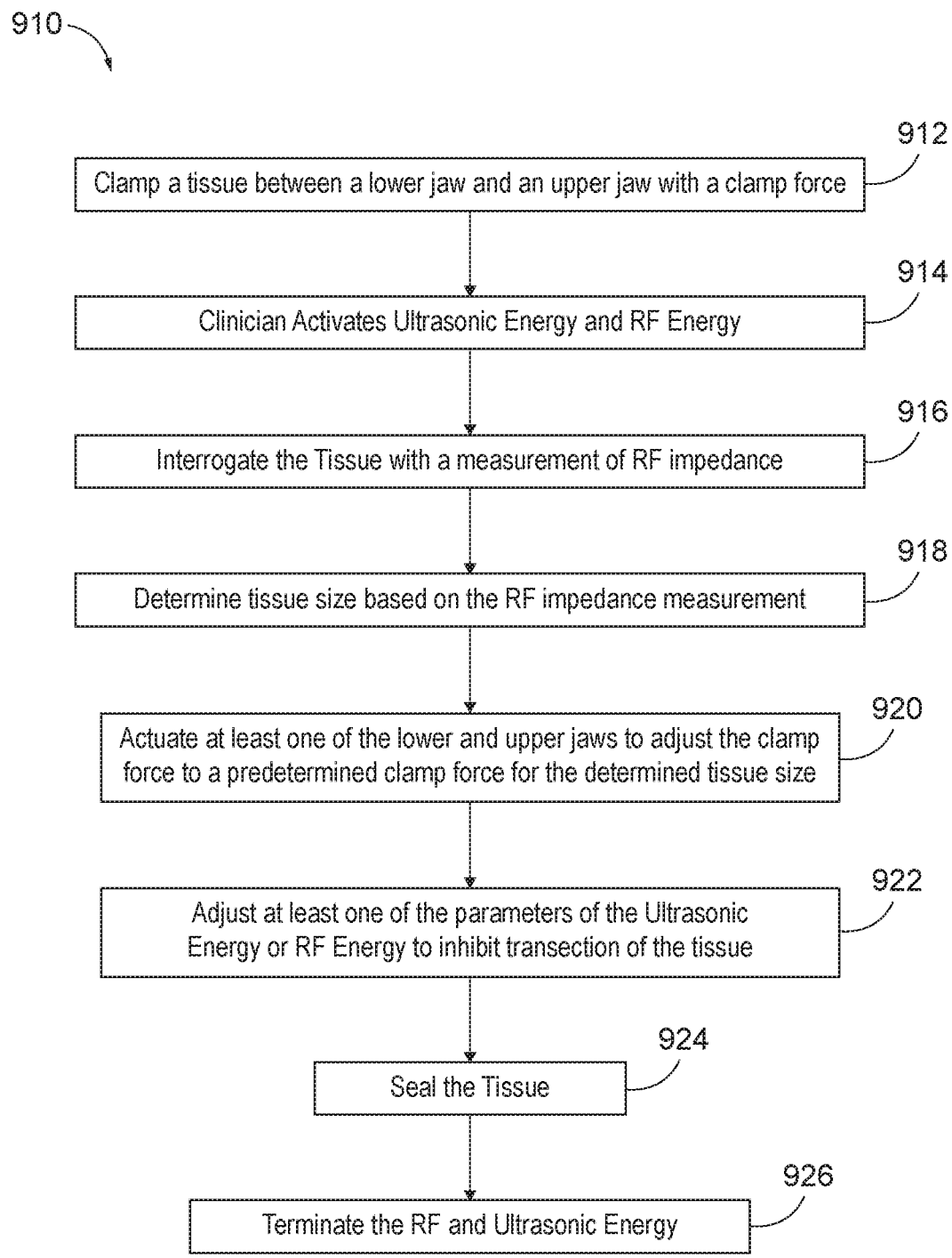
FIG. 18 depicts a flowchart of a seventh exemplary version of implementation the method of FIG. 7 with a clamp force adjustment.

Based on the RF impedance (or other electrical response) and/or tissue size determined in step (834), controller (46) sets various parameter caps that seal the vessel while inhibiting transection of the tissue. First, in the event that the vessel is small, controller (46) sets a small tissue voltage cap to the activated ultrasonic and RF energies in a step (836) and seals the small tissue in a following step (838). One exemplary small tissue voltage cap is 45 volts. Second, in the event that the vessel is medium, controller (46) sets a medium tissue voltage cap to the activated ultrasonic and RF energies in a step (840) and seals the medium tissue in a following step (842). Third, in the event that the vessel is large, controller (46) sets a large tissue voltage cap to the activated ultrasonic and RF energies in a step (844) and seals the large tissue in a following step (844). One example large tissue voltage cap is 55 volts. Once the small, medium, or large vessel is sealed in one of respective step (838), step (842), or step (846), controller (46) directs ultrasonic and RF energies to terminate in a step (848).

vi. Seventh Exemplary Version of Interrogating and Sealing Tissue with Clamp Force Adjustment FIG. 18 illustrates a seventh exemplary version for a method (910) of interrogating and sealing tissue with operating surgical system (10) of FIG. 1. The clinician first clamps the tissue between lower jaw, such as ultrasonic blade (28), and upper jaw, such as clamp arm, (26) with a clamp force in a step (912). Following clamping of the tissue in step (912), the clinician activates RF energy and ultrasonic energy on the tissue in accordance with a step (914). Controller (46) then interrogates the tissue with a measurement of RF impedance in a step (916) followed by determining the vessel size of the tissue based on the RF impedance measurement in a step (918). Alternatively, another measurement and/or information may be so used for a similar determination of vessel size similar to step (918).

Generally, higher clamp forces correlate to larger tissue clamped between ultrasonic blade (28) and clamp arm (26), and lower clamp forces correlate to smaller tissue clamped between ultrasonic blade (28) and clamp arm (26). In addition, higher clamp forces tend to increase the likelihood of inadvertently transecting the tissue with applied ultrasonic and RF energies, whereas lower clamp forces tend to decrease the likelihood of inadvertently transecting the tissue, but risk failing to properly seal the tissue. Accordingly, predetermined correlations of small, medium, and large tissue to a predetermined clamp force and electrical parameters are configured to effectively seal the tissue while inhibiting transection of the tissue.

In the present example, following the size determination of step (918), at least one of ultrasonic blade (28) and clamp arm (26) actuates relative to the other to adjust the clamp force to the predetermined clamp force in a step (920). Furthermore, controller (46) then adjusts at least one of the electrical parameters of the ultrasonic energy or the RF energy in further inhibit transection of the tissue in accordance with the predetermined correlations in a step (922). Ultrasonic and RF energies continued to be applied until the tissue is sealed in a step (924), at which time controller (46) then terminates the ultrasonic and RF energies to the tissue in a step (926).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of sealing a tissue with a surgical instrument including an ultrasonic blade and an RF electrode respectively configured to deliver an ultrasonic energy and an RF energy to the tissue, comprising: (a) interrogating the tissue with an electrical signal via at least one of the ultrasonic blade or the RF electrode to provide a tissue feedback; and (b) adjusting an electrical parameter of at least one of the ultrasonic energy or the RF energy in response to the tissue feedback to inhibit transecting the tissue.

Example 2

The method of Example 1, further comprising: (a) driving at least one of the ultrasonic blade or the RF electrode respectively with ultrasonic energy or RF energy; (b) sealing the tissue; and (c) terminating the ultrasonic energy or the RF energy respectively from the at least one of the ultrasonic blade or the RF electrode to thereby inhibit transecting the sealed tissue.

Example 3

The method of Example 2, wherein driving at least one of the ultrasonic blade or the RF electrode further includes simultaneously driving each of the ultrasonic blade and the RF electrode respectively with ultrasonic energy and RF energy.

Example 4

The method of any one or more of Examples 3 through 4, wherein terminating the ultrasonic energy or the RF energy further includes simultaneously terminating the ultrasonic energy and the RF energy respectively to the ultrasonic blade and the RF electrode thereby inhibiting transecting the sealed tissue.

Example 5

The method of any of any one or more of Examples 1 through 4, further comprising: (a) measuring an RF impedance of the tissue; (b) comparing the measured RF impedance of the tissue to a predetermined RF impedance; and (c) determining that the tissue is sealed based on the comparison of the measured RF impedance to the predetermined RF impedance.

Example 6

The method of any one or more of Examples 1 through 5, further comprising determining a relative size of the interrogated tissue.

Example 7

The method of Example 6, wherein determining the relative size of the interrogated tissue further includes: (a) measuring RF tissue impedance with a low frequency RF interrogation; and (b) comparing the measured RF tissue impedance to a predetermined data for a plurality of tissue sizes.

Example 8

The method of Example 6, further comprising decreasing an ultrasonic drive current of the ultrasonic energy.

Example 9

The method of Example 6, wherein determining the relative size further includes determining that the relative tissue size is a small tissue or a medium tissue, the method further comprising: (a) setting a power cap; (b) comparing the measured tissue impedance to a low termination impedance; and (c) determining whether the measured tissue impedance is greater than or equal to the low termination impedance.

Example 10

The method of Example 6, wherein determining the relative size further includes determining that the relative tissue size is a large tissue, the method further comprising: (a) setting a power cap; (b) comparing the measured tissue impedance to a high termination impedance; and (c) determining whether the measured tissue impedance is greater than or equal to the high termination impedance.

Example 11

The method of Example 6, further comprising: (a) measuring a first collective power of ultrasonic energy and RF energy; (b) measuring a second collective power of ultrasonic energy and RF energy after the measured first collective power; (c) measuring a first tissue RF impedance; (d) measuring a second tissue RF impedance after the measured first tissue RF impedance; and (e) calculating a normalized change in energy based on the first and second collective power differential normalized by the first and second tissue RF impedances.

Example 12

The method of Example 11, further comprising: (a) comparing the normalized change in energy to a predetermined data for a plurality of vessel sizes; and (b) setting the ultrasonic energy to an ultrasonic energy cap based on the determined tissue size.

Example 13

The method of Example 6, further comprising: (a) measuring an initial RF impedance of the tissue; (b) measuring a minimum RF impedance of the tissue; and (c) setting the ultrasonic energy to an ultrasonic energy cap based on the determined tissue size based on the initial or minimum RF impedance of the tissue.

Example 14

The method of Example 6, further comprising: (a) identifying an initial RF impedance from the measured RF impedance and an associated initial RF impedance time; (b) identifying a minimum RF impedance from the measured RF impedance and an associated minimum RF impedance time; and (c) setting a voltage cap based the determined tissue size.

Example 15

The method of Example 6, further comprising: (a) clamping the tissue between a lower jaw and an upper jaw with a clamp force, wherein one of the lower and upper jaws includes the ultrasonic blade; and (b) actuating at least one of the lower jaw or the upper jaw to thereby adjust the clamp force to a predetermined clamp force.

Example 16

An ultrasonic surgical instrument, comprising: (a) an end effector configured to actuate from a first configuration to a second configuration, including: (i) an ultrasonic blade configured to selectively to apply ultrasonic energy to a tissue, and (ii) an RF electrode configured to selectively to apply RF energy to the tissue, wherein the RF electrode is further configured to measure a tissue impedance of the tissue engaged by the end effector; (b) a shaft assembly projecting proximally from the end effector; (c) a body projecting proximally from the shaft assembly, wherein the body includes an energy input operatively connected to the ultrasonic blade; and (d) a power controller operatively connected to the ultrasonic blade, the RF electrode, and the energy input, wherein the power controller is configured to selectively direct activation of at least one of the ultrasonic blade or the RF electrode, wherein the power controller is further configured to interrogate the tissue with an electrical signal via at least one of the ultrasonic blade or the RF electrode to provide a tissue feedback, and wherein the power controller is further configured to adjust an electrical parameter of at least one of the ultrasonic energy or the RF energy in response to the tissue feedback to inhibit transecting the tissue.

Example 17

The ultrasonic surgical instrument of Example 16, wherein the power controller is further configured to terminate the ultrasonic energy or the RF energy respectively from the at least one of the ultrasonic blade or the RF electrode to thereby inhibit transecting the sealed tissue.

Example 18

The ultrasonic surgical instrument of any one or more of Examples 16 through 17, wherein the power controller has a predetermined RF impedance stored thereon and is further configured to measure an RF impedance of the tissue, compare the measured RF impedance of the tissue to the predetermined RF impedance, and determine whether the tissue is sealed based on the comparison between the measured RF impedance and the predetermined RF impedance.

Example 19

The ultrasonic surgical instrument of any one or more of Examples 16 through 18, wherein the power controller is further configured to determine a relative size of the interrogated tissue based on the tissue feedback.

Example 20

An ultrasonic surgical instrument, comprising: (a) an end effector configured to actuate from a first configuration to a second configuration, including: (i) an ultrasonic blade configured to selectively apply ultrasonic energy to tissue, (ii) a jaw movably positioned relative to the ultrasonic blade and configured to move between an open position and a closed position, wherein the jaw and ultrasonic blade in the open position are configured to receive tissue, and wherein the jaw and ultrasonic blade in the closed position are configured to clamp tissue with a clamp force, and (iii) an RF electrode configured to selectively apply RF energy to a tissue clamped within the end effector, wherein the RF electrode is further configured to measure a tissue impedance of a tissue clamped within the end effector; (b) a shaft assembly projecting proximally from the end effector; (c) a body projecting proximally from the shaft assembly, wherein the body includes an energy input operatively connected to the ultrasonic blade; and (d) a power controller operatively connected to the jaw and having a predetermined clamp force stored, wherein the power controller is configured to measure the clamp force applied between the ultrasonic blade and the jaw with tissue therein and actuate the jaw relative to the ultrasonic blade such that the clamp force adjusts to the predetermined clamp force.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

Any one or more of the teaching, expressions, embodiments, examples, etc. described herein may be combined with any one or more of the teachings, expressions, embodiments, examples, etc. described in U.S. patent application Ser. No. 15/967,758, entitled "Combination Ultrasonic and Electrosurgical Instrument with Clamp Arm Position Input and Method for Identifying Tissue State," filed on even date herewith, issued as U.S. Pat. No. 11,229,473 on Jan. 25, 2022; U.S. patent application Ser. No. 15/967,770, entitled "Combination Ultrasonic and Electrosurgical Instrument with Adjustable Clamp Force and Related Methods," filed on even date herewith, published as U.S. Pub. No. 2018/0333187 on Nov. 22, 2018; U.S. patent application Ser. No. 15/967,775, entitled "Combination Ultrasonic and Electrosurgical Instrument with Adjustable Energy Modalities and Method for Limiting Blade Temperature," filed on even date herewith, issued as U.S. Pat. No. 11,229,474 on Jan. 25, 2022; U.S. patent application Ser. No. 15/967,777, entitled "Combination Ultrasonic and Electrosurgical Instrument and Method for Sealing Tissue with Various Termination Parameters," filed on even date herewith, issued as U.S. Pat. No. 11,229,475 on Jan. 25, 2022; and/or U.S. patent application Ser. No. 15/967,784, entitled "Combination Ultrasonic and Electrosurgical Instrument and Method for Sealing Tissue in Successive Phases," filed on even date herewith, published as U.S. Pub. No. 2018/0333190 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on even date herewith, issued as U.S. Pat. No. 11,234,750 on Feb. 1, 2022; U.S. patent application Ser. No. 15/967,746, entitled "Combination Ultrasonic and Electrosurgical Instrument Having Slip Ring Electrical Contact Assembly," filed on even date herewith, issued as U.S. Pat. No. 10,945,778 on Mar. 16, 2021; U.S. patent application Ser. No. 15/967,747, entitled "Combination Ultrasonic and Electrosurgical Instrument Having Electrically Insulating Features," filed on even date herewith, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on even date herewith, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on even date herewith, issued as U.S. Pat. No. 11,058,472 on Jul. 13, 2021; U.S. patent application Ser. No. 15/967,759, entitled "Combination Ultrasonic and Electrosurgical Instrument Having Ultrasonic Waveguide With Distal Overmold Member," filed on even date herewith, issued as U.S. Pat. No. 11,051,866 on Jul. 6, 2021; U.S. patent application Ser. No. 15/967,761, entitled "Combination Ultrasonic and Electrosurgical System Having Generator Filter Circuitry," filed on even date herewith, published as U.S. Pat. No. 2018/0333184 on Nov. 22, 2018; and/or U.S. patent application Ser. No. 15/967,764, entitled "Combination Ultrasonic and Electrosurgical System Having EEPROM and ASIC Components," filed on even date herewith, issued as U.S. Pat. No. 11,129,661 on Sep. 28, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention is understood not to be limited to the details of structure and operation shown and described in the specification and drawings.

We claim:

1. A method of sealing a tissue with a surgical instrument including an end effector having an ultrasonic blade and a radiofrequency (RF) electrode respectively configured to deliver an ultrasonic energy and an RF energy to the tissue, comprising:
   (a) interrogating the tissue with an electrical signal via the end effector to provide a tissue feedback;
   (b) adjusting an electrical parameter of the end effector in response to the tissue feedback to inhibit transecting the tissue;
   (c) measuring a first collective power of the ultrasonic energy and the RF energy;
   (d) measuring a second collective power of the ultrasonic energy and the RF energy after the measured first collective power;
   (e) measuring a first tissue RF impedance;
   (f) measuring a second tissue RF impedance after the measured first tissue RF impedance; and
   (g) calculating a normalized change in energy based on a differential between the first collective power of ultrasonic energy and RF energy and the second collective power of ultrasonic energy and RF energy normalized by the first tissue RF impedance and the second tissue RF impedance for sealing the tissue with the end effector.

2. The method of claim 1, further comprising:
   (a) driving at least one of the ultrasonic blade or the RF electrode respectively with ultrasonic energy or RF energy;
   (b) sealing the tissue; and
   (c) terminating the ultrasonic energy or the RF energy respectively from the at least one of the ultrasonic blade or the RF electrode to thereby inhibit transecting the sealed tissue.

3. The method of claim 2, wherein driving at least one of the ultrasonic blade or the RF electrode further includes simultaneously driving each of the ultrasonic blade and the RF electrode respectively with ultrasonic energy and RF energy.

4. The method of claim 3, wherein terminating the ultrasonic energy or the RF energy further includes simultaneously terminating the ultrasonic energy and the RF energy respectively to the ultrasonic blade and the RF electrode thereby inhibiting transecting the sealed tissue.

5. The method of claim 1, further comprising:
   (a) measuring a third RF impedance of the tissue;
   (b) comparing the measured third RF impedance of the tissue to a predetermined RF impedance; and
   (c) determining that the tissue is sealed based on the comparison of the measured third RF impedance to the predetermined RF impedance.

6. The method of claim 1, further comprising determining a relative size of the interrogated tissue.

7. The method of claim 6, wherein determining the relative size of the interrogated tissue further includes:
   (a) measuring a third RF tissue impedance with a low frequency RF interrogation; and
   (b) comparing the measured third RF tissue impedance to a predetermined data for a plurality of tissue sizes.

8. The method of claim 6, further comprising decreasing an ultrasonic drive current of the ultrasonic energy.

9. The method of claim 6, wherein determining the relative size further includes determining that the relative tissue size is a small tissue or a medium tissue, the method further comprising:
   (a) setting a power cap;
   (b) comparing a third measured tissue impedance to a low termination impedance; and
   (c) determining whether the third measured tissue impedance is greater than or equal to the low termination impedance.

10. The method of claim 6, wherein determining the relative size further includes determining that the relative tissue size is a large tissue, the method further comprising:
    (a) setting a power cap;
    (b) comparing a third measured tissue impedance to a high termination impedance; and
    (c) determining whether the third measured tissue impedance is greater than or equal to the high termination impedance.

11. The method of claim 6, further comprising:
    (a) measuring an initial RF impedance of the tissue;
    (b) measuring a minimum RF impedance of the tissue; and
    (c) setting the ultrasonic energy to an ultrasonic energy cap based on the determined relative size of the interrogated tissue based on the initial or minimum RF impedance of the tissue.

12. The method of claim 6, further comprising:
    (a) identifying an initial RF impedance from a measured third RF impedance and an associated initial RF impedance time;
    (b) identifying a minimum RF impedance from the measured third RF impedance and an associated minimum RF impedance time; and
    (c) setting a voltage cap based the determined relative size of the interrogated tissue.

13. The method of claim 6, further comprising:
    (a) clamping the tissue between a lower jaw and an upper jaw with a clamp force, wherein one of the lower and upper jaws includes the ultrasonic blade; and
    (b) actuating at least one of the lower jaw or the upper jaw to thereby adjust the clamp force to a predetermined clamp force.

14. The method of claim 1, further comprising:
    (a) comparing the normalized change in energy to a predetermined data for a plurality of vessel sizes; and
    (b) setting the ultrasonic energy to an ultrasonic energy cap based on the determined relative size of the interrogated tissue.

15. The method of claim 1, wherein the ultrasonic blade and the RF electrode are operatively connected to a controller, and wherein the controller calculates the normalized change in energy.

16. A method of sealing a tissue with a surgical instrument including an ultrasonic blade and a radiofrequency (RF) electrode respectively configured to deliver an ultrasonic energy and an RF energy to the tissue, comprising:
    (a) interrogating the tissue with an electrical signal via the end effector;
    (b) measuring a first collective power of ultrasonic energy and RF energy;

(c) measuring a second collective power of ultrasonic energy and RF energy after the measured first collective power;
(d) measuring a first tissue RF impedance;
(e) measuring a second tissue RF impedance after the measured first tissue RF impedance;
(f) calculating a normalized change in energy based on the first and second collective power differential normalized by the first and second tissue RF impedances; and
(g) sealing the tissue based on the calculated normalized change in energy.

17. The method of claim 16, further comprising determining a relative size of the interrogated tissue.

18. The method of claim 17, further comprising:
(a) comparing the normalized change in energy to a predetermined data for a plurality of vessel sizes; and
(b) setting the ultrasonic energy to an ultrasonic energy cap based on the determined relative size of the interrogated tissue.

19. A method of sealing a tissue with a surgical instrument including an ultrasonic blade and a radiofrequency (RF) electrode respectively configured to deliver an ultrasonic energy and an RF energy to the tissue, wherein the ultrasonic blade and the RF electrode are operatively connected to a controller and a data circuit, wherein the data circuit includes a first collective power of ultrasonic energy and RF energy measured at the tissue and stored thereon, a second collective power of ultrasonic energy and RF energy measured at the tissue after the measured first collective power and stored thereon, a first tissue RF impedance measured at the tissue and stored thereon, a second tissue RF impedance measured at the tissue after the measured first tissue RF impedance and stored thereon, the method comprising:
(a) accessing each of the first collective power of ultrasonic energy and RF energy, the second collective power of ultrasonic energy and RF energy, the first tissue RF impedance, and the second tissue RF impedance from the data circuit via the controller; and
(b) calculating a normalized change in energy based on a differential between the first collective power of ultrasonic energy and RF energy and the second collective power of ultrasonic energy and RF energy normalized by the first tissue RF impedance and the second tissue RF impedance, wherein the controller calculates the normalized change in energy for sealing the tissue with the end effector.

20. The method of claim 19, further comprising:
(a) comparing the normalized change in energy to a predetermined data for a plurality of vessel sizes;
(b) determining a relative size of the interrogated tissue; and
(b) setting the ultrasonic energy to an ultrasonic energy cap based on the determined relative size of the interrogated tissue.

* * * * *